(12) United States Patent
Yasaka et al.

(10) Patent No.: US 6,753,499 B1
(45) Date of Patent: Jun. 22, 2004

(54) METHOD AND APPARATUS FOR DETECTING ANOMALOUS DISCHARGE IN PLASMA PROCESSING EQUIPMENT USING WEAKLY-IONIZED THERMAL NON-EQUILIBRIUM PLASMA

(75) Inventors: Mitsuo Yasaka, Kumamoto (JP); Masayoshi Takeshita, Kumamoto (JP)

(73) Assignees: Japan Science and Technology Corporation, Saitama (JP); part interest; Kumamoto Technopolice Foundation, Kumamoto (JP); part interest ( * ) Notice: Subject to any disclaimer, the term of this patent is extended or adjusted under 35 U.S.C. 154(b) by 0 days.

(21) Appl. No.: 09/980,379
(22) PCT Filed: Mar. 28, 2001
(86) PCT No.: PCT/JP01/02536
§ 371 (c)(1),
(2), (4) Date: Nov. 28, 2001
(87) PCT Pub. No.: WO01/74123
PCT Pub. Date: Oct. 4, 2001

(30) Foreign Application Priority Data

Mar. 28, 2000 (JP) ....................................... 2002/089840

(51) Int. Cl.⁷ .............................................. B23K 10/00
(52) U.S. Cl. ........................... 219/121.59; 219/121.43; 374/117
(58) Field of Search ........................ 219/121.59, 121.43, 219/69.16, 69.13; 374/117; 324/409; 156/345.28; 204/298.03, 298.32; 73/597

(56) References Cited

U.S. PATENT DOCUMENTS 4,582,974 A * 4/1986 Itoh ........................ 219/69.13

(List continued on next page.)

FOREIGN PATENT DOCUMENTS

| CN | 2296285 | 11/1998 |
|---|---|---|
| GB | 2 230 993 | 11/1990 |
| JP | 52-143882 | 11/1977 |

(List continued on next page.)

OTHER PUBLICATIONS

Lundgaard et al., Nov. 1990, Acoustic Diagnosis of Gas Insulated Substations: A Theoretical and Experimental Basis IEEE Transactions on Power Delivery, vol. 5, Nov. 4.

(List continued on next page.)

Primary Examiner—Quang T. Van
(74) Attorney, Agent, or Firm—McGlew and Tuttle, P.C.

(57) ABSTRACT

An anomalous arc discharge detection apparatus, including multiplicity of ultrasonic detectors placed at different sections of a plasma processing chamber such that an ultrasonic wave accompanying an anomalous discharge is detected by the ultrasonic detectors at different propagation times or with different delay times. The detected signals are compared with each other on the same time axis to obtain the maximum range of variation of the detected waveforms and the differences in delay time of the respective ultrasonic detectors. From the comparison of the maximum range of variation and the delay times of the ultrasonic detectors, the position of the source point, and the level as well, of the anomalous arc discharge are determined, which can be displayed on a monitor and utilized to issue an alarm if necessary. The position of the anomalous discharge may be obtained by an asymptotic approximation based on recursive calculations of the distances from the source point to the respective ultrasonic detectors using formulas which define the distances in terms of the delay times. This can be done using only four ultrasonic detectors arranged on the wall of the processing chamber. An AE sensor hold case is provided to accommodate an AE sensor. The hold sensor has a lower cover which has one end to be glued onto an appropriate position of the processing chamber, and an upper cover which pushes the AE sensor against the lower cover with an adequate pressure.

26 Claims, 21 Drawing Sheets

U.S. PATENT DOCUMENTS

| | | | |
|---|---|---|---|
| 4,588,952 A | * | 5/1986 | Matsuoka .................... 324/409 |
| 4,602,142 A | * | 7/1986 | Itoh ......................... 219/69.13 |
| 4,635,198 A | | 1/1987 | Hohlweck et al. |
| 5,810,963 A | | 9/1998 | Tomioka |
| 6,234,023 B1 | * | 5/2001 | Collins et al. ................. 73/597 |

FOREIGN PATENT DOCUMENTS

| | | |
|---|---|---|
| JP | 60-60506 | 4/1985 |
| JP | 62-32364 | 2/1987 |
| JP | 92-294921 | 12/1987 |
| JP | 3-501827 | 4/1991 |
| JP | 06-265338 | 9/1994 |
| JP | 07-055874 | 3/1995 |
| JP | 08-220076 | 8/1996 |
| JP | 09-145346 | 6/1997 |
| JP | 10-074734 | 3/1998 |

OTHER PUBLICATIONS

Lee et al., Dec. 1998, Estimation of Partial Discharge Parameters in GIS Using Acoustic Emission Techniques: A Theoretical Approach Journal of Computational Acoustics, vol. 6, No. 4.

R. T. Harrold, 1980, Acoustic Emission Signature of Arcs and Sparks IEEE International Symposium on Electrical Insulation (pp. 184–189).

* cited by examiner

NEWTON'S METHOD FOR SOLVING $f(x)=0$

METHOD AND APPARATUS FOR DETECTING ANOMALOUS DISCHARGE IN PLASMA PROCESSING EQUIPMENT USING WEAKLY-IONIZED THERMAL NON-EQUILIBRIUM PLASMA

TECHNICAL FIELD

The invention relates to an apparatus and a method therefor for detecting anomalous discharges accompanying a plasma discharge generated by a high-frequency voltage across a pair of electrodes supplied by a dc power source or a high-frequency power source. The invention also relates to an acoustic emission (AE) sensor hold case.

BACKGROUND ART

Today's semiconductor manufacturing industries widely use plasma discharge processing in chemical vapor deposition (CVD), ashing, etching, and sputtering of semiconductor substrates, as well as in surface processing thereof. Anomalous plasma discharges take place in a plasma processing equipment, which cause for example creation of dusts, damaging and/or contamination of semiconductor substrates, and electric breakdown of the electronic components on the substrates. In order to deal with these problems associated with anomalous discharges, accurate detection of occurrence and accurate determination of the location of an anomalous plasma discharge is necessary. There have been made extensive researches for a method to detect such anomalous discharges, which include detection of a change in the intensity of light emitted by the plasma, a change in the voltage and/or the current through a power supply, a change in plasma impedance, and a change of harmonic across the electrodes.

However, when monitoring the fluctuation in a plasma radiation for an anomalous discharge in a plasma processing equipment, relevant portions generating the plasma are covered with deposit shields if the frequency of the plasma is high. Therefore, it is necessary to modify many of the mounting equipment for the optical fibers. On the other hand, if the optical fiber is successfully mounted on the apparatus, characteristics of the plasma can be altered by the optical fiber. Process chambers having a viewing window also have a drawback in that accurate determination of the location of an anomalous discharge is difficult, since the entire plasma region cannot be observed through the viewing port.

A method of detecting an anomalous discharge through monitoring changes in the supply voltage of an RF power supply and/or the current though it, and in the plasma impedance, fails complete detection of the anomalous discharge. Furthermore, in this method, complete locations of the anomalous discharge cannot be known, since anomalous discharges can take place outside the electrodes. Although generation of an anomalous discharge can be attained by detecting changes in the harmonics modes of the plasma, the method cannot determine the positions of the discharges. Thus, presently there is no method known which is capable of both detecting anomalous discharges and determining the locations thereof.

In addition, there is a need for a method and means therefor for allowing easy mounting and dismounting of ultrasonic detection means (e.g. AE sensors) during maintenance, and preventing destruction and deterioration of the AE sensors caused by the stresses during mounting/dismounting of the sensors, thereby attaining a high precision ultrasonic detection of anomalous discharges by the AE sensors.

DISCLOSURE OF INVENTION

In search of adequate physical parameters which can be of good indication of an anomalous plasma discharge in a plasma discharge processing equipment, the inventors found a fact that ultrasonic waves accompany such anomalous plasma discharges and that they can be used as an indication of anomalous plasma discharges.

It is therefore an object of the invention to provide a method and an apparatus therefor for detecting anomalous plasma discharges in a plasma processing equipment by detecting an ultrasonic wave emitting from an anomalous discharge by means of ultrasonic detectors.

It is another object of the invention to provide a method and an apparatus therefor for accurately determining the position (hereinafter also referred to as source point) of an anomalous discharge in a plasma generating apparatus by means of multiple ultrasonic detectors placed at predetermined positions in the apparatus.

It is a further object of the invention to provide an apparatus which can estimate the level of the anomalous discharge by measuring the energy of an accompanying ultrasonic wave; display the location of the anomalous discharge detected; and generate an alarm if the level of the anomalous discharges exceeds a predetermined threshold level.

It is a still further object of the invention to provide convenient means for installing ultrasonic detectors on a plasma processing equipment.

To the accomplishment of the foregoing objects, there is provided an anomalous plasma discharge detection apparatus in accordance with one aspect of the invention, the apparatus comprising:

ultrasonic detection means, in the form of acoustic emission (AE) sensors for example, for detecting an ultrasonic wave accompanying an anomalous plasma discharge in a plasma processing equipment and for generating signals indicative of the ultrasonic wave detected (hereinafter referred to as ultrasonic signals;

data processing means for processing said ultrasonic signals; and monitor means for displaying the signals.

The anomalous plasma discharge detection apparatus may comprise a multiplicity of ultrasonic detection means, such as AE sensors, mounted on different components of a plasma processing equipment such as a vacuum chamber and electrodes for forming a plasma, for detecting the location of the anomalous plasma discharge in the vacuum chamber for example, the anomalous plasma discharge detection apparatus adapted to locate the source point by comparing on the same time axis the waveforms of an ultrasonic wave detected by these detection means to calculate delays in detection time (hereinafter referred to as delay times) by the respective ultrasonic detection means with respect to the first detection time by one of the detection means.

The anomalous plasma discharge detection apparatus may have only four ultrasonic detection means installed on the walls of a plasma processing chamber of the plasma processing equipment, such that the source point of the anomalous plasma discharge can be determined by an asymptotic approximation thereof through recursive calculations of the distances from the source point to the respective detection means in relation to the differences in delay time of the ultrasonic wave detected by the respective ultrasonic detection means.

The anomalous plasma discharge detection apparatus can be adapted to determine the level (or intensity) of an ultrasonic wave accompanying an anomalous plasma discharge, and also adapted to issue an alarm when the level is excessively high.

It is noted that the ultrasonic detection means may be provided with electrically insulated mounting means for mounting the ultrasonic detection means on the plasma processing equipment in an electrically insulated condition.

In another aspect of the invention, there is provided a method of detecting an anomalous plasma discharge in a plasma processing equipment by detecting an ultrasonic wave accompanying the anomalous plasma discharge.

In a still further aspect, the invention provides a method of locating the source point of an anomalous discharge in a plasma processing equipment by recursive calculations of the distances between the source point and four ultrasonic detection means based on the differences in delay time for the four ultrasonic detection means, the method using an asymptotic approximation of the source point through the recursive calculations thereof.

In a further aspect of the invention, the invention provides a dedicated hold case for accommodating and securing in position an acoustic emission (AE) sensor so that the AE sensor is in forced abutment against the lower case by an adequate pressure, thereby allowing an ultrasonic wave generated by an anomalous discharge to be transmitted to the AE sensor across their contacting surfaces. The hold case has a removable upper cover. With this apparatus, AE sensors can be glued on several positions of a processing chamber of a plasma processing equipment, especially on an existing apparatus, much easier than mounting them on the processing chamber without forming mounting bores. In addition, gluing the AE sensors on the processing chamber provides a better acoustic coupling between them. Further, when the sensors need to be removed from the apparatus for maintenance purposes for example, they can be easily removed by hitting them. Accordingly, the hitting may result in destruction of the AE sensors and deterioration of the internal structure, thereby failing to improve reproducibility of mounting the AE sensor.

BRIEF DESCRIPTION OF THE DRAWINGS

The invention will now be described in detail by way of example with reference to accompanying drawings, in which like parts having like reference numerals are the same or corresponding elements throughout the drawings.

BEST MODE FOR CARRYING OUT THE INVENTION

Figure 1A:
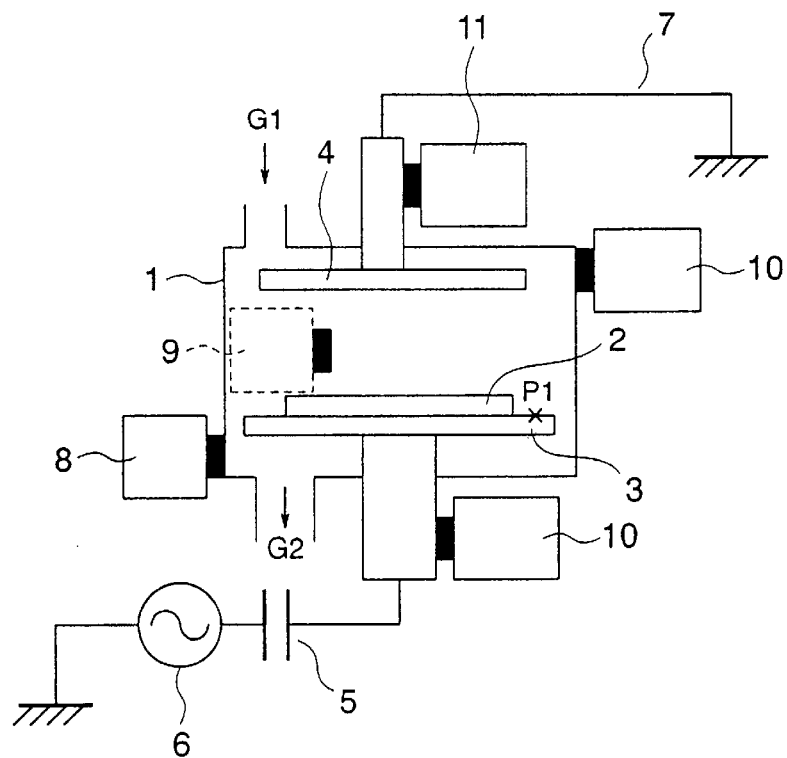
FIG. 1A shows an exemplary plasma processing equipment, and FIG. 1B an arrangement of detectors of an apparatus for detecting an anomalous plasma discharge in a plasma processing equipment in accordance with the invention. Such detectors and apparatus will be hereinafter referred to as anomalous plasma discharge detectors or discharge detectors, and anomalous plasma detection apparatus, respectively.

The invention will now be described in detail by way of example with reference to accompanying drawings, in which like reference numerals indicate like parts.

Figure 1B:
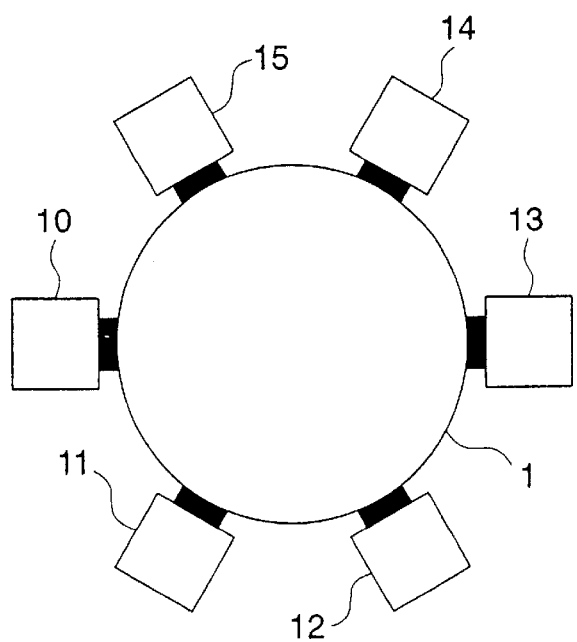

FIG. 1 shows, in cross section (FIG. 1A) and in top view (FIG. 1B), an arrangement of ultrasonic detection means of an anomalous plasma discharge detection apparatus according to the invention, set up for a plasma processing equipment generating plasmas.

Figure 2:
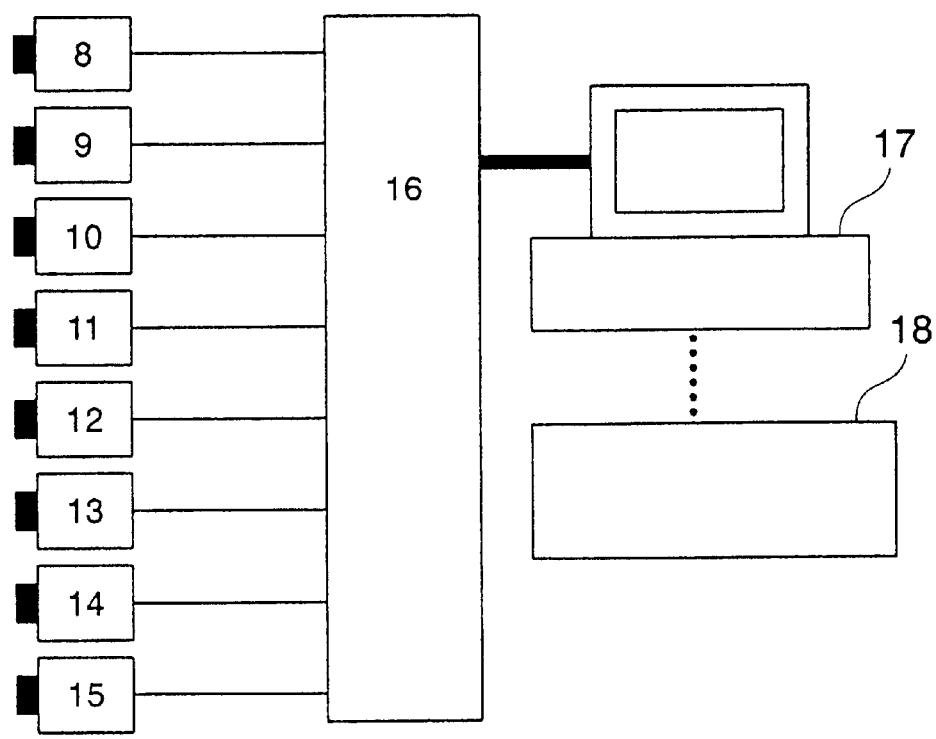
FIG. 2 is a schematic diagram illustrating an anomalous plasma discharge detection apparatus according to the invention.

FIG. 2 shows a principle of the anomalous discharge detection apparatus of the invention. As shown in FIG. 1A. the plasma processing equipment includes a processing chamber 1, a wafer 2 placed in the processing chamber 1 for plasma processing thereof, a lower electrode 3 for mounting thereon the wafer 2, an upper electrode 4 facing the lower electrode 3, a blocking condenser 5, an RF power source (high-frequency power source) 6 connected to the lower electrode 3 via the blocking condenser 5, and a ground line 7. Injection and exhaustion of a gas are indicated by arrows G1 and G2, respectively.

The anomalous plasma discharge detection apparatus shown in FIGS. 1A and 1B is provided with a multiplicity of ultrasonic detectors 8–15. The detection apparatus shown in FIG. 1 is an example which has eight ultrasonic detectors such that the ultrasonic detector 8 is mounted on the lower electrode 3, ultrasonic detector 9 on the upper electrodes 4, and six ultrasonic detectors 10–15 are mounted on the upper and the lower sections of the exterior side walls, angularly spaced apart by 60° along the circumference. The anomalous plasma discharge detection apparatus of FIG. 2 has an A/D converter 16, a computer 17, and an anomalous discharge generation/location indicator 18 for indicating the occurrence of an anomalous discharge and the location of the anomalous discharge.

As shown in FIG. 2, the ultrasonic detectors 8–15 detect an ultrasonic wave to generate detection signals, which are converted into digital signals by the AD converter 16 and supplied to the computer 17. The computer 17 processes and stores the digital signals, determines if an anomalous discharge has occurred, and if it has, determines the source point of the anomalous discharge and issues an alarm for the plasma processing equipment. An anomalous discharge location/alarm indicator 18 is provided to indicate the location of the detected anomalous discharge along with an alarm on a monitor.

Figure 3:
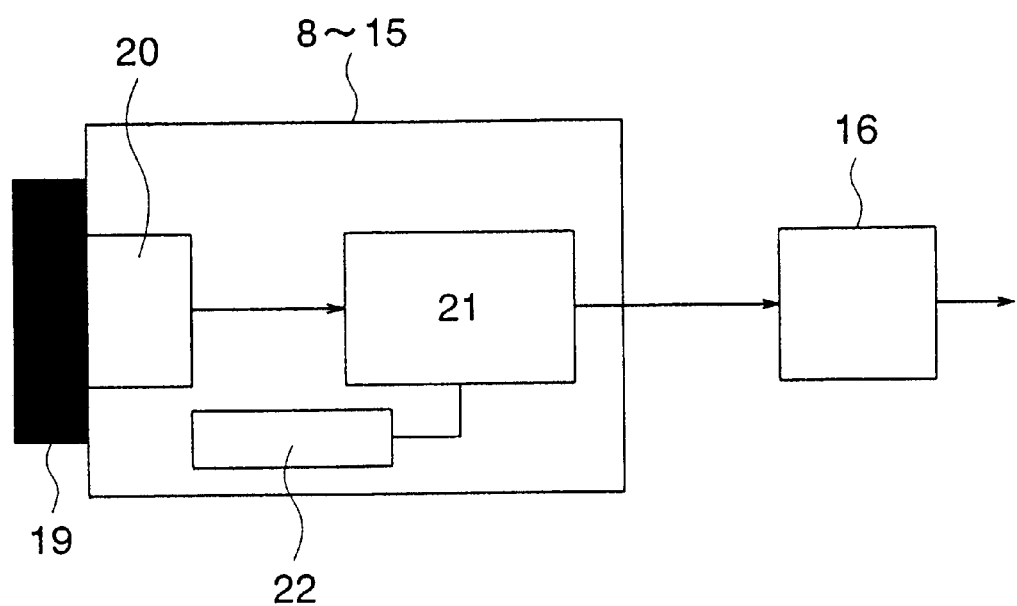
FIG. 3 is a schematic diagram of an anomalous plasma discharge detector in the form of an ultrasonic detector according to the invention.

FIG. 3 shows an arrangement of any of the ultrasonic detectors 8–15 according to the invention. As shown in FIG. 3, the ultrasonic detector includes: an electrically insulative member (ceramic) 19 coated with a couplant which provides desirable acoustic connection between the ultrasonic detector and the processing chamber; an ultrasonic conversion element 20; an amplifier 21; and a battery 22. By physically connecting the couplant-coated insulation member 19 of the ultrasonic detector to the processing chamber 1 as shown in FIGS. 1A and 1B, ultrasonic waves can be transmitted to the ultrasonic detector without inducing any electric noises.

Figure 4:
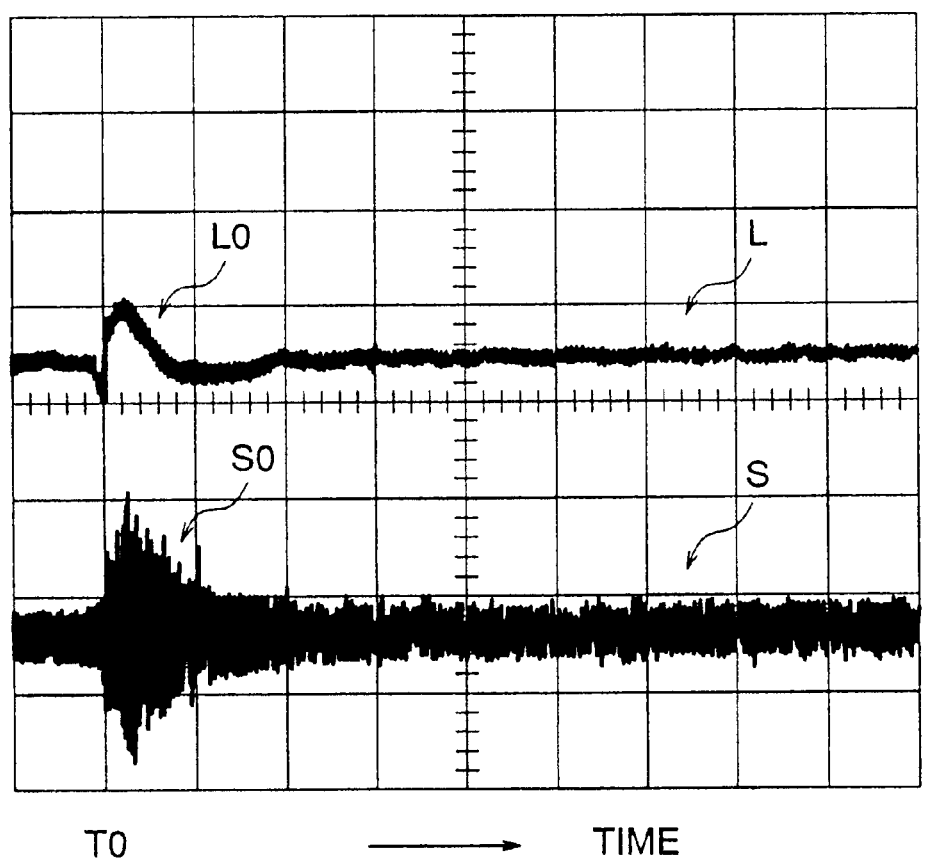
FIG. 4 shows waveforms of ultrasonic waves detected by the ultrasonic detector of FIG. 3.

FIG. 4 shows a typical waveform L detected by a photosensor and a waveform S detected by an ultrasonic detector of the invention, which were observed by the inventors while studying anomalous discharges in the plasma processing equipment. The anomalous fluctuation in plasma radiation detected by the photosensor manifests occurrence of anomalous plasma discharge. It is seen that the output power S0 of the ultrasonic detector varies in the same manner as the radiation by the anomalous plasma discharge during a period L0. This indicates generation of ultrasonic waves accompanying the anomalous plasma discharge. It was confirmed by the inventors that an ultrasonic wave of about 25 kHz is generated during such anomalous discharge. It was also confirmed that the birth of an ultrasonic wave accompanying an anomalous plasma discharge has a lag behind the fluctuation of radiation, which lag depends on the location of the discharge, and that the frequency and the maximum range of variation of the ultrasonic waveforms (or equivalently the range of variation of a waveform or the height of a waveform) varies with the intensity of the radiation by an anomalous plasma discharge.

It is considered that the an ultrasonic wave accompanying an anomalous plasma discharge is caused by the bombardment of charged particles (e.g. electrons) generated in the anomalous discharge onto the constituent components (e.g. upper electrodes 4) of the plasma processing equipment, or by destruction of surface layers of the components. Thus, when an anomalous plasma discharge takes place at some location, acoustic emission (AE) of ultrasonic waves results in at that location. Accordingly, the energy $\mu$ of an AE event determines the degree of destruction of the surface layers subject to the anomalous discharge. It is therefore important to determine $\mu$.

Measured maximum range of variation Vpp of the ultrasonic wave is related to the energy $\mu$ of the AE event by the following formula.

$$Vpp^2 = C_1 \cdot C_2 \mu \tag{1}$$

where $C_1$ is a constant which depends on the detection sensitivity of the ultrasonic detector used, and $C_2$ is a constant which depends on the distance from the source point of the anomalous discharge to the ultrasonic detector, and the energy loss during the propagation over that distance.

Based on this formula, it is possible to find permissible levels of damage and contamination of the surface of a substrate under plasma processing, contamination of the substrate, and the maximum range of variation Vpp of the ultrasonic wave affecting dielectric breakdown of the electronic components on the substrate due to the anomalous plasma discharge, so that upon detection of an excessive anomalous discharge an alarm may be issued and displayed.

The propagation time T for the ultrasonic wave to reach an ultrasonic detector is given by $$T = D/V \tag{2}$$

where V is the speed of the ultrasonic wave, which depends on the materials forming the processing chamber 1, and D the distance from the source point of the anomalous discharge to the detector.

Therefore, if a multiplicity of ultrasonic detectors are provided at different positions of the plasma processing equipment, the location of the anomalous discharge, i.e. the source point, can be determined from the different propagation times to the respective detectors.

Figure 8:
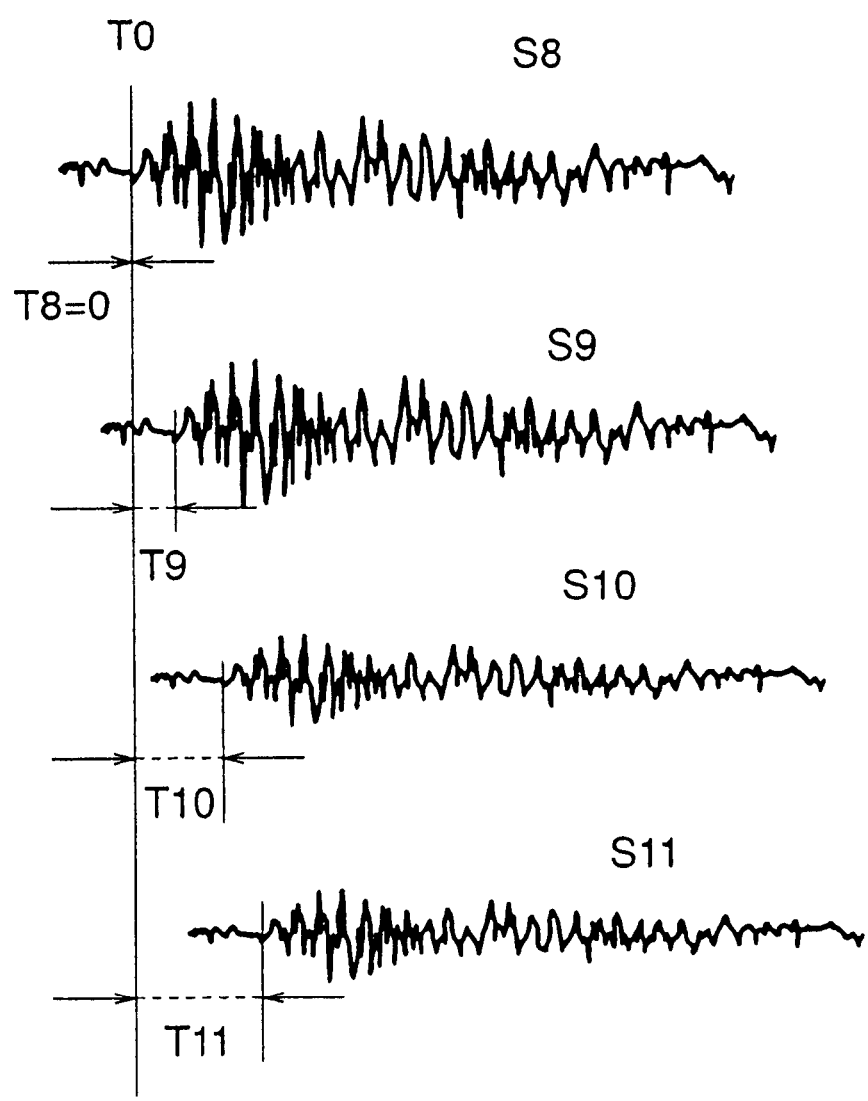
FIG. 8 shows waveforms of an ultrasonic wave detected by the respective ultrasonic detectors arranged as shown in FIGS. 6A and 6B.

The invention converts the analog signals detected by the ultrasonic detectors 8–15 to digital signals by an A/D converter 16, and processes the digital data by a computer 17, as shown in FIG. 2. Since the frequency and the amplitude of an ultrasonic wave generated in an AE event depend on the energy of the AE event and the materials involved in the AE event, the invention compares the waveforms of the ultrasonic waves detected by the ultrasonic detectors 8–15 on the same time axis when the amplitude of these waveforms exceed a predetermined magnitude. From the comparison, relative propagation times of the ultrasonic wave to the respective detectors 8–15, or delay times, with respect to the first detection time by one of the detectors, can be calculated. The maximum range of variation (as shown in FIG. 8) of these waves can be also determined.

The inventive method of locating the source point of an anomalous plasma discharge in the plasma processing equipment can be described as follows. The method includes a procedure for determining whether the source point is on the upper electrode or the lower electrode, or determining the position of the source point on the side wall. First, waveforms output from the ultrasonic detectors 10–15 are compared with each other to find a reference ultrasonic detector, which is one detecting the ultrasonic wave first. From the comparison, delay times T10–T15 for the respective detectors 10–15 with respect to the reference ultrasonic detector are also calculated.

Figure 5:
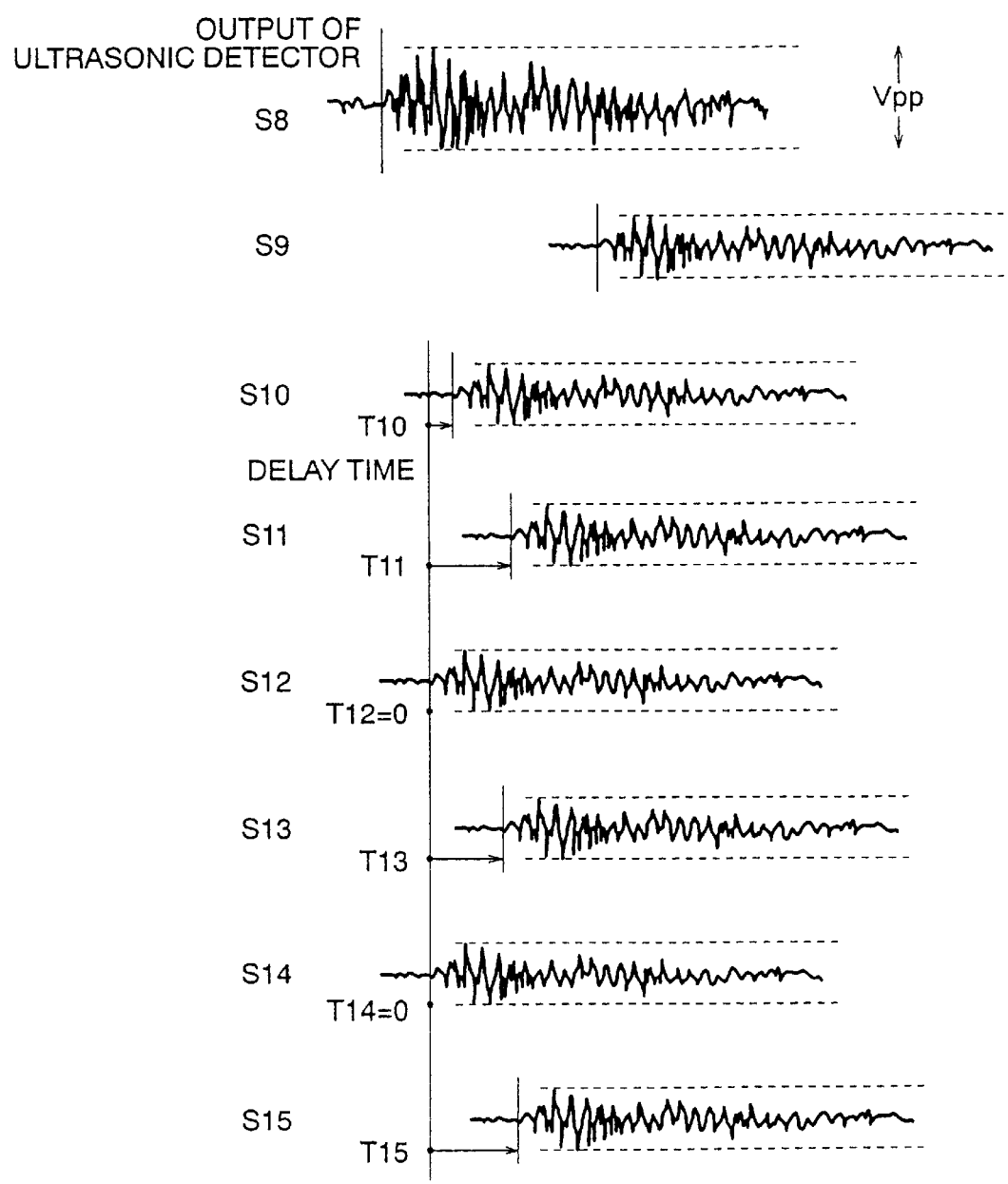
FIG. 5 shows waveforms of an ultrasonic wave arising from an anomalous plasma discharge occurring at a lower electrode of a plasma processing equipment, as detected by the respective ultrasonic detectors arranged as shown in FIG. 1B.

For example, suppose that an anomalous discharge takes place at the lower electrode 3 (position P1 in FIG. 1). Then the waveforms output from the respective ultrasonic detectors appear like ones as shown in FIG. 5. When the ultrasonic detectors 10, 12, 14 are positioned at the same distance from a support 3A of the lower electrode, detection of the ultrasonic wave by the ultrasonic detector 10 lags behind those of the ultrasonic detectors 12 and 14 by an amount of time to travel across the support 3A, so that the reference detector is either the ultrasonic detector 12 or the ultrasonic detector 14, for which the delay time is zero.

Treating the side wall of the processing chamber as a 2-dimensional plane, the following simultaneous equations hold for the coordinates of a discharge point (source point) (x, y) and the coordinates (X10, Y10)–(X15, Y15) of the ultrasonic detectors 10–15, respectively.

$$V^2(t+T10)^2=(x-X10)^2+(y-Y10)^2 \quad (3.1)$$

$$V^2(t+T11)^2=(x-X11)^2+(y-Y11)^2 \quad (3.2)$$

$$V^2(t+T12)^2=(x-X12)^2+(y-Y12)^2 \quad (3.3)$$

$$V^2(t+T13)^2=(x-X13)^2+(y-Y13)^2 \quad (3.4)$$

$$V^2(t+T14)^2=(x-X14)^2+(y-Y14)^2 \quad (3.5)$$

$$V^2(t+T15)^2=(x-X15)^2+(y-Y15)^2 \quad (3.6)$$

where T is the time for an ultrasonic wave to travel from the discharging point to the reference ultrasonic detector, and V is the speed of the ultrasonic wave.

If the solution (x, y) for the equations represents a point inside the side walls, the source point of the anomalous discharge must be inside the side wall. Otherwise, the discharge source point is outside the side wall. If the source point is determined from these six equations to be anywhere other than the side wall, then the location of the anomalous discharge is considered to be either on the upper or the lower end wall of the plasma processing equipment. This can be determined from the known position of the reference ultrasonic detector and the delay times measured by the ultrasonic detector 8 mounted on the lower electrode 3 and detector 9 on the upper electrode 4.

Figure 9A:
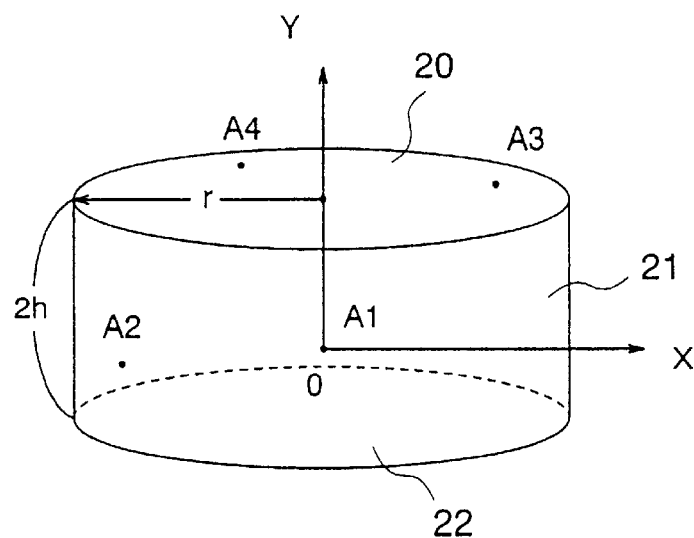
FIGS. 9A and 9B show, in 3-dimensional view (FIG. 9A) and in 2-dimensional view (FIG. 9B), sub-regions of a plasma processing chamber for calculating four possible locations (or source points) of an anomalous plasma discharge.
Figure 9B:
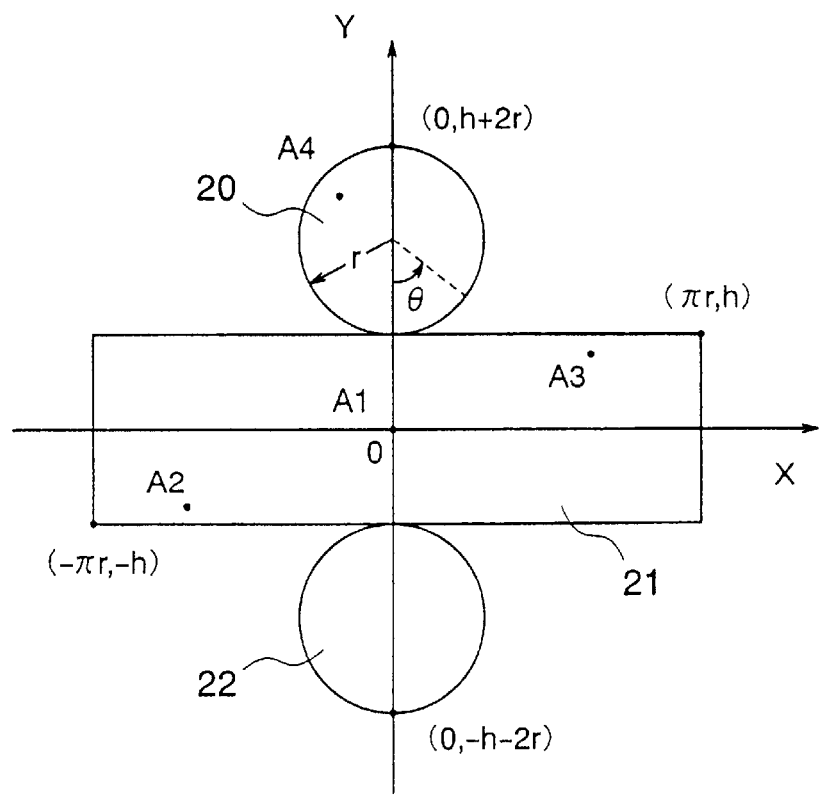

If the reference ultrasonic detector is either one of the ultrasonic detectors 10, 12, or 14 mounted on the lower end of the side wall, and if the ultrasonic detector 8 has detected the wave earlier than the detector 9, then the source point is determined to be in the lower section of the plasma processing equipment (FIG. 5). Under these conditions, the three simultaneous equations (3.1), (3.3), (3.5) for the three ultrasonic detectors 10, 12, and 14 are solved, treating the lower end of the processing chamber 1 coplanar with the side wall as shown in FIG. 9B. When the solution represents a position on the support 3A of the lower electrode 3 lying on the lower end of the processing chamber, it is determined that the source point is on the lower electrode 3, but otherwise, the source point is determined to lie on the lower end of, and inside, the processing chamber.

When the reference ultrasonic detector is either one of the ultrasonic detectors 11, 13, and 15 mounted on the upper end of the side wall, and if the detector 9 detects the wave earlier than the detector 8, it is determined that the discharging source point is in the upper section of the plasma processing chamber. In this case, the three simultaneous equations (3.2), (3,4) and (3.6) for the ultrasonic detectors 11, 13, and 15 are solved, treating the upper end of the processing chamber 1 as co-planar with the side wall. If the solved position is anywhere other than the support 4A of the upper electrode 4 in the upper section of the processing chamber 1, the discharging source is determined to be on the inner upper end of the processing chamber, but otherwise to be on the upper electrode 4.

The precision of locating the discharge source point may be improved by providing more ultrasonic detectors at different positions. For example, if additional ultrasonic detectors are mounted on the upper and lower electrodes, the very position of the source points on the electrodes may be determined.

A characteristic delay time may be computed by the computer 17 by, for example, averaging characteristic delay times associated with characteristic indices of the waves (e.g. height of the waveforms during an anomalous discharge).

A lookup table may be provided in a memory which defines correspondence between possible locations of the anomalous discharge source point and the patterns of delay times for particular arrangement of the ultrasonic detectors so that, given waveforms of the detected ultrasonic waves, the computer 17 analyzes the delay time pattern to determine the location of the source point with respect to the ultrasonic detectors.

Upon determination of the anomalous discharge source point, the constant $C_2$ of the equation (1), and hence the energy $\mu$ of the AE event, is obtained, since the respective propagation distances and the attenuation losses for these distances are known. From the location and the maximum range of variation of the detected ultrasonic wave thus determined, the level of the acoustic emission (AE) during the anomalous discharge is determined and displayed on a monitor. An alarm may be generated and/or the operation of the processing apparatus may be stopped when the amplitudes of the wave detected by the respective detectors exceed predetermined levels set for respective locations of the plasma processing equipment.

In the example shown in FIG. 1, the peripheries of upper and lower end walls of the processing chamber are divided into three equal parts and a total of six ultrasonic detectors are arranged one for each part such that any two detectors do not face-to-face, to thereby detect and locate the source point of an anomalous discharge in the processing chamber.

In actuality, however, in the method shown in FIG. 1, more than six detectors (eight detectors in the example shown in FIG. 1) are required, since further detectors are needed on the upper and the lower end walls as well, which results in additional cost. Furthermore, it is difficult to find a proper arrangement of these detectors.

The inventors have found a further method different from the method of FIG. 1, in which only four detectors are required to determine the location of an anomalous discharge source point.

Figure 6A:
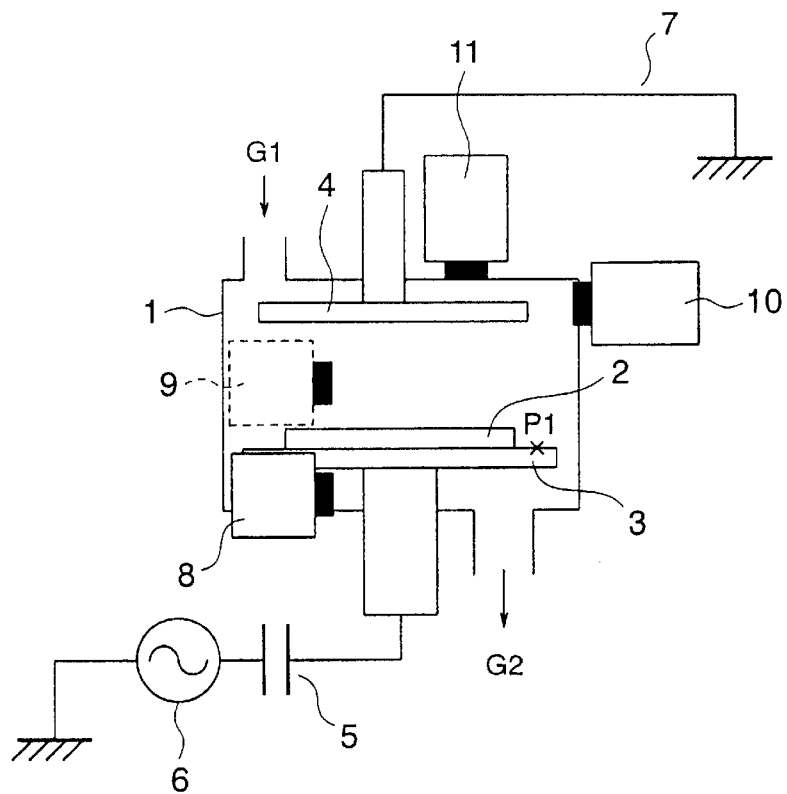
FIGS. 6A and 6B show an exemplary arrangement of an anomalous discharge detection apparatus having four anomalous discharge detectors, in a side elevation (FIG. 6A) and in a plan view (FIG. 6B).
Figure 6B:
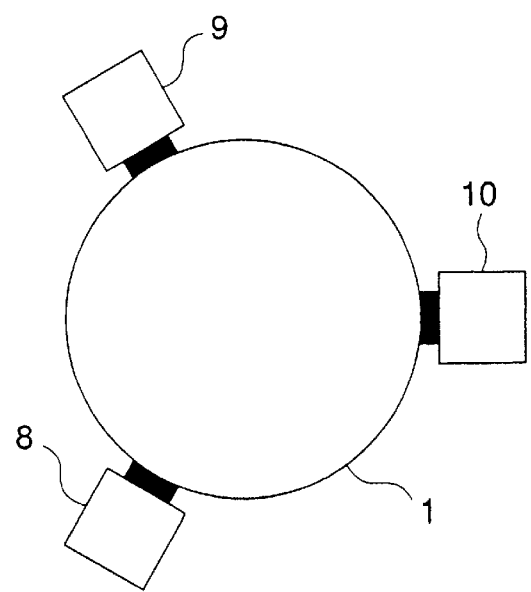
Figure 7:
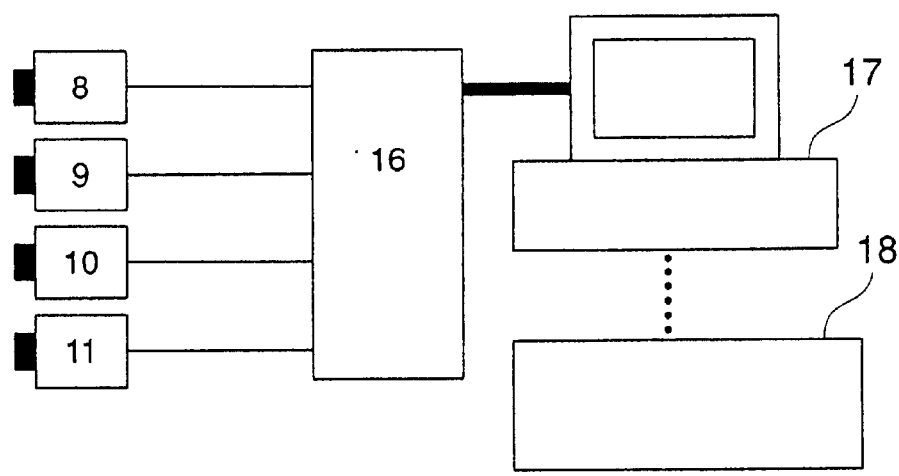
FIG. 7 is a schematic view of an anomalous plasma discharge detection apparatus having four anomalous discharge detectors for detecting the location of an anomalous discharge.

Referring to FIGS. 6 through 18, the further method using four ultrasonic detectors will now be described. FIG. 6A shows an example in which ultrasonic detectors are arranged in a plasma processing equipment based on this method. FIG. 6B shows in cross sectional view an arrangement of ultrasonic detectors mounted on the processing chamber 1 at the intermediate level thereof FIG. 7 shows an exemplary anomalous discharge detection apparatus which utilizes four ultrasonic detectors. It is noted that like reference numerals refer to the same elements in FIGS. 1 through 5, so that the description of each element will not be repeated here unless otherwise needed.

FIG. 8 compares the outputs S8–S11 of the ultrasonic detectors 8–11 as shown in FIG. 6 when their amplitudes exceed a threshold level. T0 is the time at which an ultrasonic wave is first detected by one of the ultrasonic detectors (the detector hereinafter referred to as reference detector); Periods T8–T11 are delay times for the respective detectors 8–11 with reference to the detection time of the reference detector.

FIG. 8 applies to a case where the anomalous discharge source point generating the ultrasonic wave is located on the lower electrode 3 (shown at P1 in FIG. 1). In this instance, the ultrasonic detector 8 is mounted on the lower section of the exterior wall of the processing chamber 1, and the ultrasonic detectors 9 and 10 on the upper section of the exterior wall. In this instance the reference detector is detector 8, for which the delay time is zero.

The source point of an anomalous discharge can be located using four ultrasonic detectors in accordance with the invention as follows. It is convenient to define a 2-dimensional XY Cartesian coordinate system to locate the position of the anomalous discharge source point. The processing chamber 1 is represented in FIG. 9A by a cylinder having a radius R and a height 2H. The XY coordinate system is defined with y axis coinciding the central axis of the cylinder and X axis coinciding a radius of the cylinder passing through the center O of the cylinder, with the origin being at the center O, as shown in FIG. 9A. FIG. 9B is an expansion plan of the processing chamber 1 onto which XY coordinate system is projected with the origin O projected onto the center of the parallelepiped side wall of the cylinder, and the upper and the lower ends 20 and 22, respectively, of the cylinder projected onto the projected y axis, as shown. The positions of the ultrasonic detectors 8–11 of FIG. 6 are marked on the XY plane by dots A1 through A4.

FIG. 6 illustrates an arrangement of ultrasonic detectors for which areas of the processing chamber are divided into four substantially equal sections as even as possible in order to attain uniform precision of measurements by the detectors.

Assume that the reference ultrasonic detector is the detector 8, and denote by D8–D11 the shortest distances from the source point of an anomalous discharge to the respective detectors 8–11, and the speed of the ultrasonic wave by V. Since the distances calculated from the delay times for the respective detectors correspond to the respective differences between the distance from the source pint to the respective detectors 8–11 and the distance from the source point to the reference detector 8, the following equations hold.

$$V \times T9 - (D9 - D8) = 0 \quad (4.1)$$

$$V \times T10 - (D10 - D8) = 0 \quad (4.2)$$

$$V \times T11 - (D11 - D8) = 0 \quad (4.3)$$

If all of the propagation paths of the ultrasonic wave from the discharge source point to the detectors 8–11 lie on the same plane (such paths hereinafter referred to as coplanar paths), the distances D8–D11 can be expressed in terms of the coordinates (x, y) of the source point, so that the equations (4.1)–(4.3) are actually a set of equations involving only two variables x and y. Hence, the coordinates (x, y) can be determined by Eq. (4.1) and (4.2).

Figure 10A:
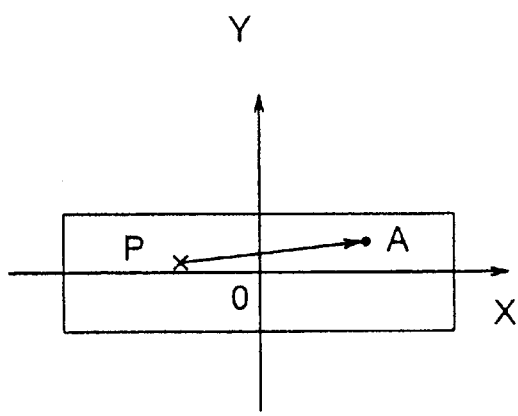
FIGS. 10A through 10D illustrate different propagation paths of an ultrasonic wave emitted from the source point of an anomalous plasma discharge to the respective ultrasonic detectors.

However, it may be a case that all the paths from the source point to the respective ultrasonic detectors are not coplanar, i.e. the paths are not on the same plane. FIGS. 10A–10D show typical cases where an ultrasonic wave propagates from an anomalous discharge source point P to an ultrasonic detector A. In particular, FIG. 10A shows a coplanar path on the side wall, FIG. 10B a non-coplanar propagation path from a point on the upper end wall of the processing chamber to a point on the side wall, FIG. 10C a non-coplanar propagation path from a point on the side wall to another point on the side wall through the upper end wall; and FIG. 10D a propagation path from a point on the upper end wall to a point on the lower end wall through the side wall.

Figure 10B:
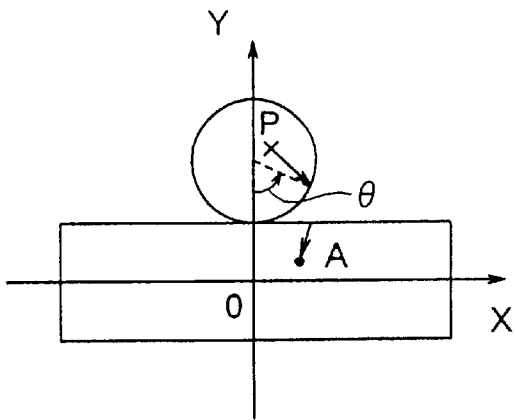

For example, in the case shown in FIG. 10B where the discharge source point P is located on the upper end wall of the processing chamber 1 and the ultrasonic detector is at position A of the side wall, the shortest path crosses the circumference of the upper end wall at a point where the radius of the upper end wall makes an angle with y axis, and the shortest distance D depends on θ as well as on the position (x, y) of the discharge source point P. Hence, the equations (4.1)–(4.3) involves θ in addition to x and y. As a result, the equations are difficult to solve. Further, the equations must be modified, loosing their generality, every time the position of the ultrasonic detector is changed.

There are several numerical methods to obtain the solution for the nonlinear equations, including Newton's method, a bisection method, and a linear inverse interpolation method. In the example shown herein, Newton's method is used to quickly obtain an accurate approximate solution.

Figure 11:
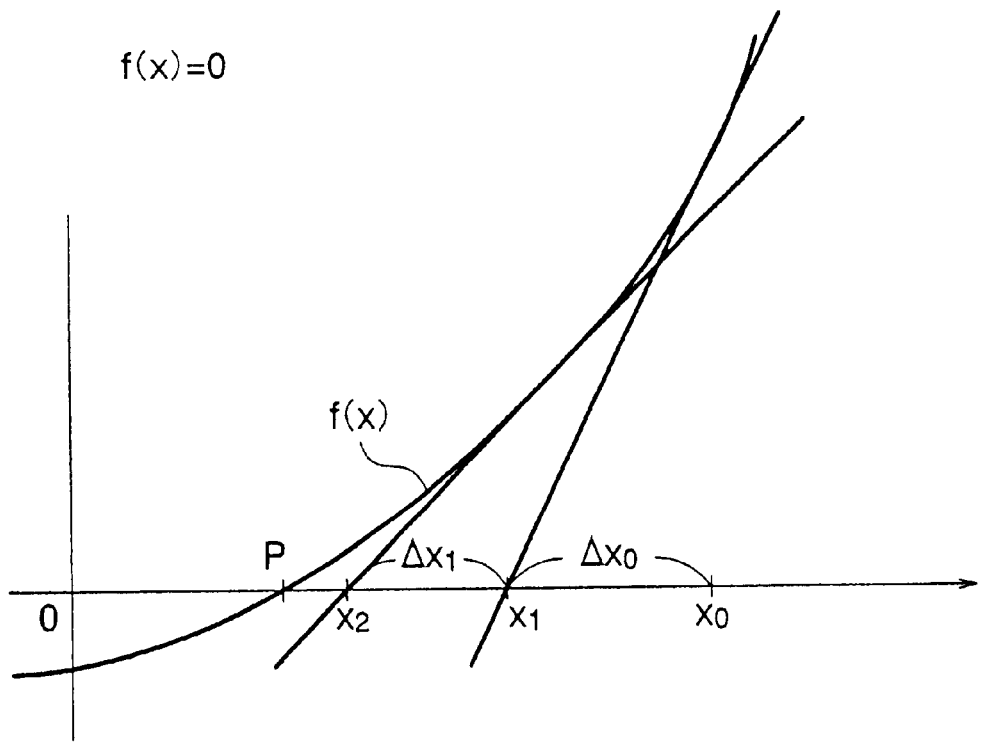
FIG. 11 depicts Newton's method of calculating the source point of an anomalous discharge according to the invention.

Referring to FIG. 11, Newton's method to obtain an approximate solution for f(x)=0 will be described. First, given an initial value $x_0$ of x, an approximate value $x_1$ is obtained from Eq. (5) below, which value is an intersection tangent off (x) at $x_0$ with X axis.

$$\Delta x_0 = x_0 - x_1 = f(x_0)/f'(x_0) \quad (5)$$

Next, a second approximate value $x_2$ for f(x)=0 is obtained from the x intersection of the tangent to the curve y=f(x) at x=$x_1$. Repeating this procedure, an asymptotic solution for f(x)=0 may be given by the limiting value of $x_0 - \Sigma \Delta x_n$, for which the absolute value of $\Delta x_{n-1} = x_{n-1} - x_n$, is arbitrarily small.

Similarly, the solutions for $f_1(x, y)=0$ and $f_2(x, y)=0$ may be given through 2-dimensional Newton's method:

$$(\partial f_1/\partial x)\Delta x + (\partial f_1/\partial y)\Delta y = f_1 \quad (6.1)$$

$$(\partial f_2/\partial x)\Delta x + (\partial f_2/\partial y)\Delta y = f_2 \quad (6.2)$$

Starting from a set of initial values $x_0$ and $y_0$ of x and y, respectively, $x_0 - \Sigma \Delta x_n$ and $y_0 - \Sigma \Delta y_n$ are recursively calculated until their absolute values become arbitrarily small.

A procedure to obtain the shortest distances D8–D11 from Eq. (4.1)–(4.3) will now be described below. Assuming that the anomalous discharging source is located on the upper end wall of the processing chamber and the initial position of the anomalous discharge source point (x, y) is arbitrarily set to ($x_0$, $y_0$) within the upper end wall section of the expansion plan shown in FIG. 9B, the shortest distance L from this source point to any one of the detectors 8–11 can be calculated by differentiating the distance L with respect to angle θ and setting the differential to 0. The shortest distance is L for that angle θ, as described in more detail below.

Denoting by g (θ) the derivative of L with respect to θ (Eq. 7), and denoting by Δθ an angular displacement in θ, the following equation may be obtained in accordance with 1-dimensional Newton's method.

$$g(\theta)=\partial L/\partial\theta=0 \tag{7}$$

$$(\partial g(\theta)/\partial\theta)\Delta\theta=g(\theta) \tag{8}$$

Figure 10C:
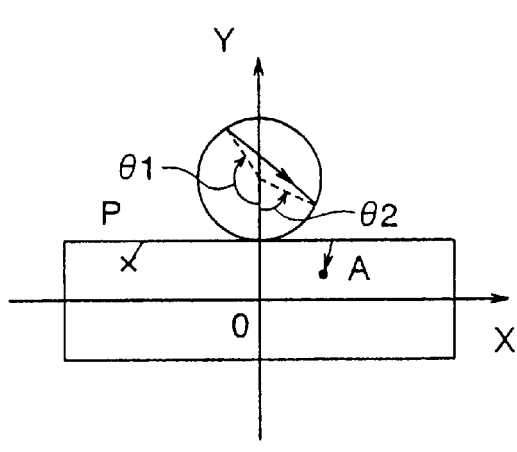
Figure 10D:
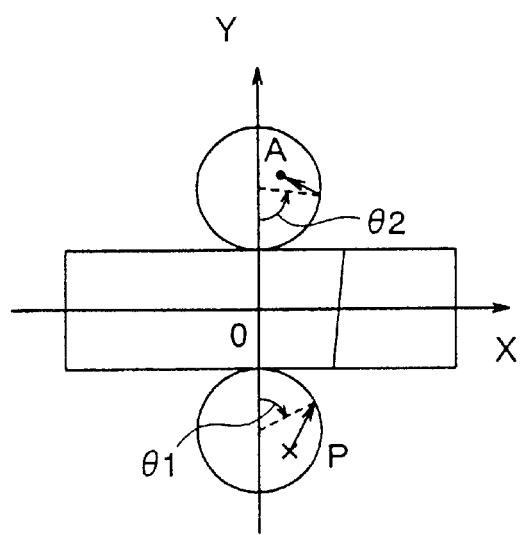

In the first step, θ is set to an arbitrary value $\theta_0$, so that the value of g(θ) is $g_0$. In the second step, a $\partial g(\theta)/\partial\theta$ is approximated by $\partial g=g_1-g_0$, where $g_1$ stands for the value of g (θ), which is obtained by adding an arbitrarily small increment $\Delta\theta_0$ to $\partial\theta_0$. Δθ is obtained by inserting the values of g (θ) and $\partial g/\partial\theta$ thus obtained in Eq. (8). This procedure is repeated by shifting θ from $\theta_0$ by Δθ until the magnitude of Δθ falls within a permissible range of error, yielding the asymptotic angle θ for the shortest path, from which the shortest distance D is obtained. In the foregoing example, the asymptotic method involves only one angle specifying the shortest propagation path from an anomalous source point to a given ultrasonic detector. The method may be applied to cases which involve two angular variables $\theta_1$, $\theta_2$, as shown in FIGS. 10C and 10D. In such cases, the shortest distance D may be obtained using the following equations.

$$g_1(\theta_1, \theta_2)=\partial L/\partial\theta_1=0 \tag{9.1}$$

$$g_2(\theta_1, \theta_2)=\partial L/\partial\theta_2=0 \tag{9.2}$$

A method of locating the source point of an anomalous discharge from the shortest distances D1–D4 and the measured delay times T8(=0) and T9–T10 will now be described below. These values are substituted in Eqs. (4.1) and (4.2) to obtain the source point. By defining the left hand sides of Eqs. (4.1) and (4.2) to be $f_1$, $f_2$, respectively, these equations can be written as $$f_1=0, f_2=0$$

where the coordinates x and y of the anomalous discharge source point are regarded as variables in $f_1$, $f_2$. The coordinates (x, y) of the source point can be obtained by applying 2-dimensional Newton's method to the simultaneous equations $f_1=0$ and $f_2=0$ to obtain asymptotic solution for (x, y), using (6.1) and (6.2). To do this, first approximate values of $\partial f_1/\partial x$, $\partial f_2/\partial x$, $\partial f_1/\partial y$, $\partial f_2/\partial y$ are calculated for small variations $\Delta x_0$ and $\Delta y_0$ at the initial coordinates ($x_0$, $y_0$), in just the same way as for the evaluation of $\partial g/\partial\theta$ in the foregoing 1-dimensional calculation of the shortest distance D, and then these values are inserted in Eqs. (6.1) and (6.2). Δx and Δy are obtained by solving the simultaneous equations $f_1=0$ and $f_2=0$. This procedure is repeated by shifting x and y from the initial values $x_0$ and $y_0$, respectively, by −Δx and −Δy, respectively, until Δx and Δy become less than a permissible error limit. It should be noted that different source points can result if the initial values $x_0$ and $y_0$ are not appropriate. To find appropriate initial values $x_0$ and $y_0$, some preliminary calculations must be made using Eqs. (6.1) and (6.2). For example, in a case where three ultrasonic detectors are positioned at a intermediate level of the plasma processing equipment and spaced apart by 60 degrees along the circumference of the side wall at that level, any anomalous discharge that takes place at any point of the plasma processing equipment can be determined correctly by choosing the initial position ($x_0$, $y_0$) at either centers of the upper and the lower end walls.

The procedure will be ended if only one source point of the anomalous discharge is found. However, if more than one source coordinates are found, a further determination of the correct source point must be determined by calculating the left hand side of Eq. (4.3) for the multiple source points obtained. The coordinates having the smallest value of the left hand side of Eq. (4.3) is determined as the correct source point. In this way, using the method of the invention, it is possible to locate a desirable asymptotic position of the source point by means of only four ultrasonic detectors.

Figure 12:
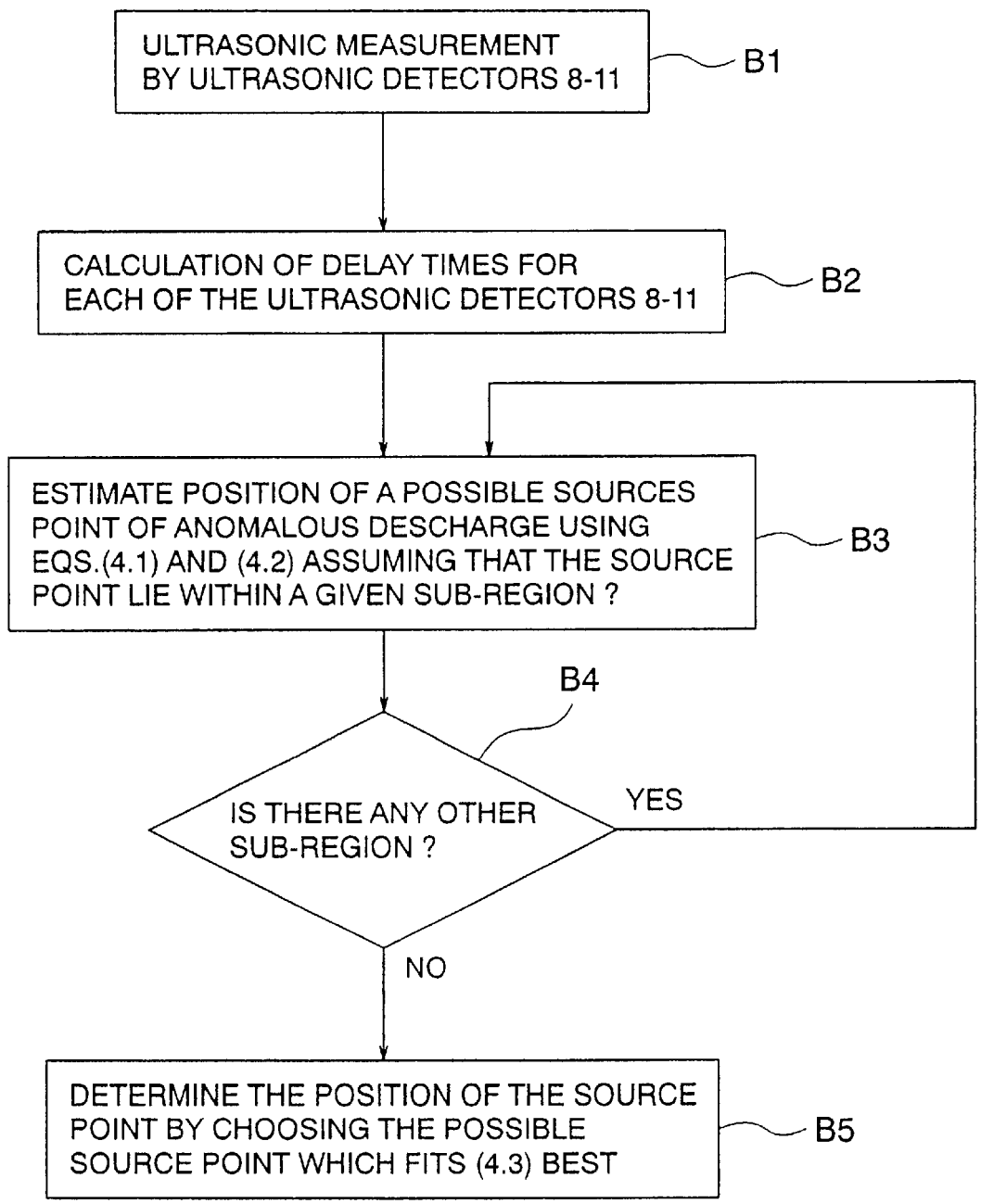
FIG. 12 is a flowchart showing a procedure of asymptotic approximation of the source point of an anomalous discharge through recursive calculations thereof based on the comparison of the waveforms detected by four anomalous discharge detectors.

As an example, determination of an anomalous discharge source point will be depicted below with reference to FIGS. 12–17. FIG. 12 is a flowchart illustrating briefly an inventive method of locating the source point of an anomalous discharge from waveforms detected by four ultrasonic detectors.

As an anomalous discharge takes place, the four ultrasonic detectors mounted on appropriate sections of the processing chamber will detect ultrasonic wave as shown in FIG. 8 (block B1). The ultrasonic detector that has first detected the ultrasonic wave at time T0 is chosen as the reference detector, and the delay times T9–T11 of the rest of the detectors relative to T0 are calculated (block B2).

It is recalled that in the asymptotic calculation of the coordinates of the source point, there is a chance that the recursive calculation does not give a unique source point, depending on the first asymptotic point chosen for the source point. To ensure that a true or correct asymptotic solution always exists among the multiple asymptotic solutions obtained for that first asymptotic point, the region of the plasma processing chamber accessible to anomalous discharges may be divided into sub-regions such that each region always has a true asymptotic source point among other possible (i.e. competing) source points, irrespective of the position of the first source point so long as a first asymptotic point is chosen within that region. Blocks B3 and B4 of FIG. 12 implies setting up of such sub-regions for different choices of the first source point. In blocks B3 and B4, all the possible source points for the sub-regions are determined by the recursive approximations by changing the first asymptotic point for each of the sub-regions.

In block B5, a true source point of the anomalous discharge is determined among the possible source points. This can be done by choosing the asymptotic point which satisfies Eq. (4.3) best as the correct source point, since the true asymptotic solution satisfies Eq. (4.3).

Figure 13:
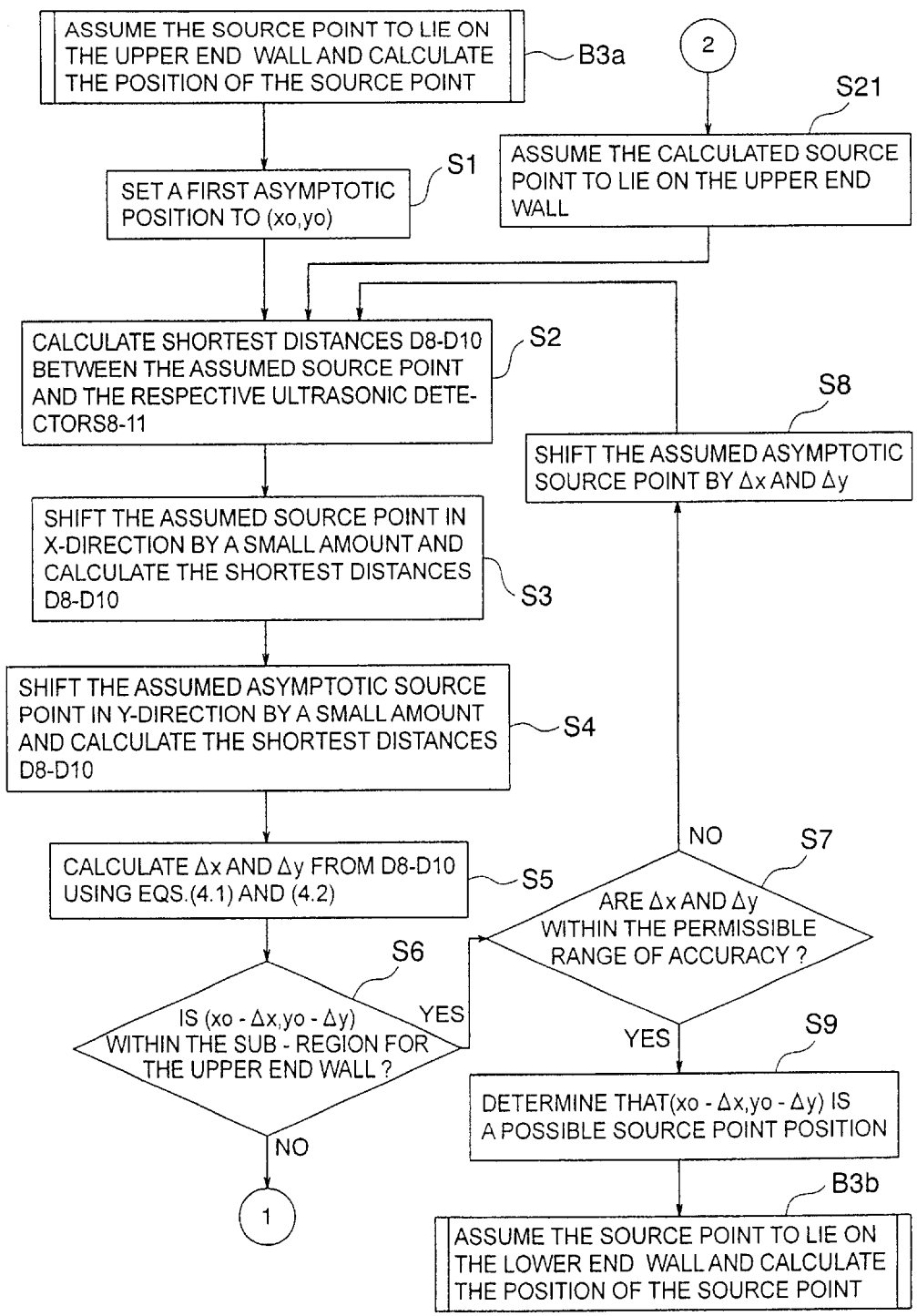
FIGS. 13 and 14 together show a specific example of the procedure shown in FIG. 12.
Figure 14:
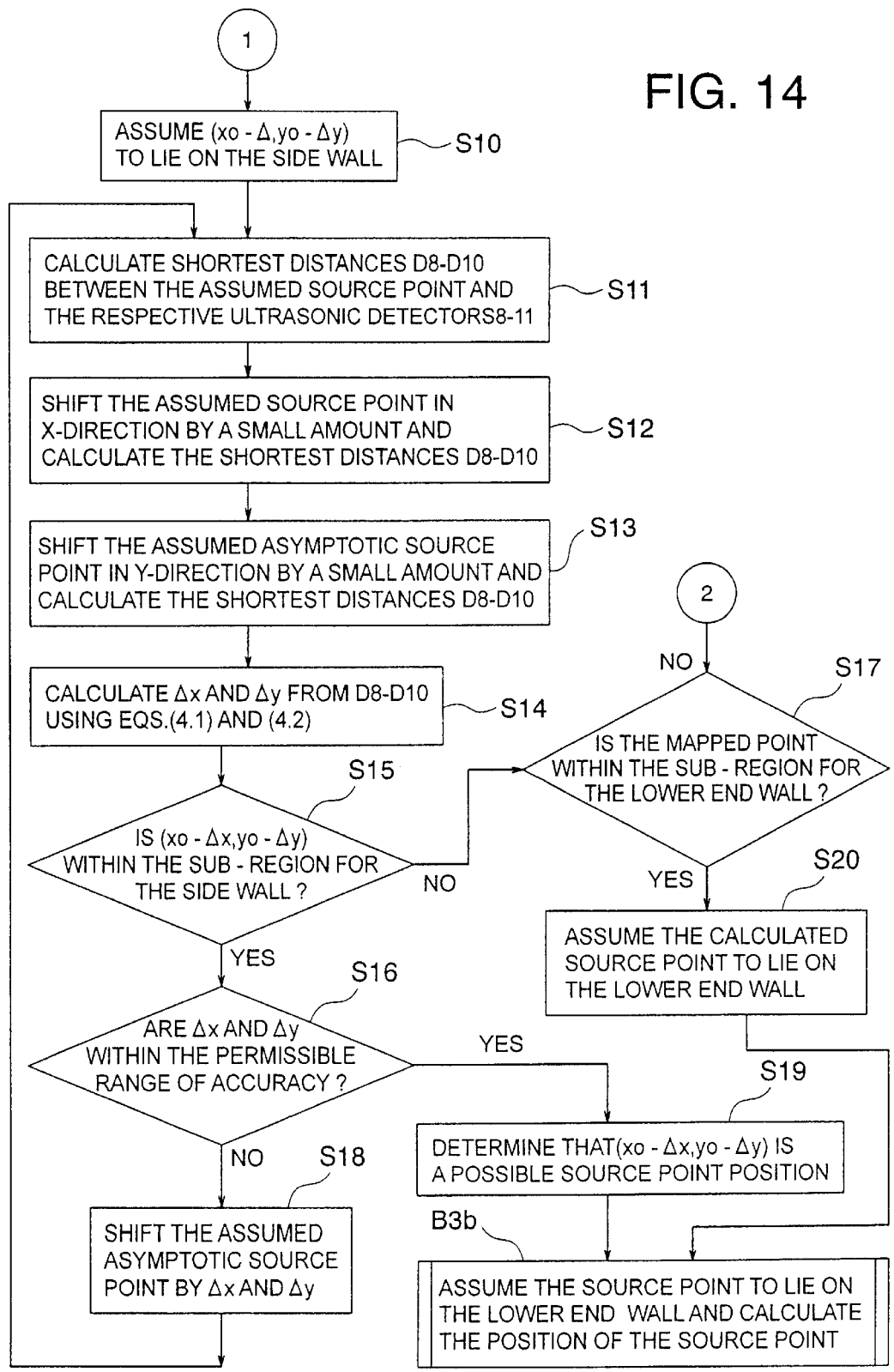

FIGS. 13 and 14 together represent a flowchart of determining correct asymptotic solution (i.e. correct source point) based on the Newton's method, by repeating the asymptotic approximation for each of the predetermined sub-regions in turn by setting up a first asymptotic point in each sub-region, for example, first in the upper end wall (block 63A), and next on the lower end wall of the processing chamber (block 64B), and so on, so long as no correct asymptotic solution is found in the current sub-region.

Figure 15:
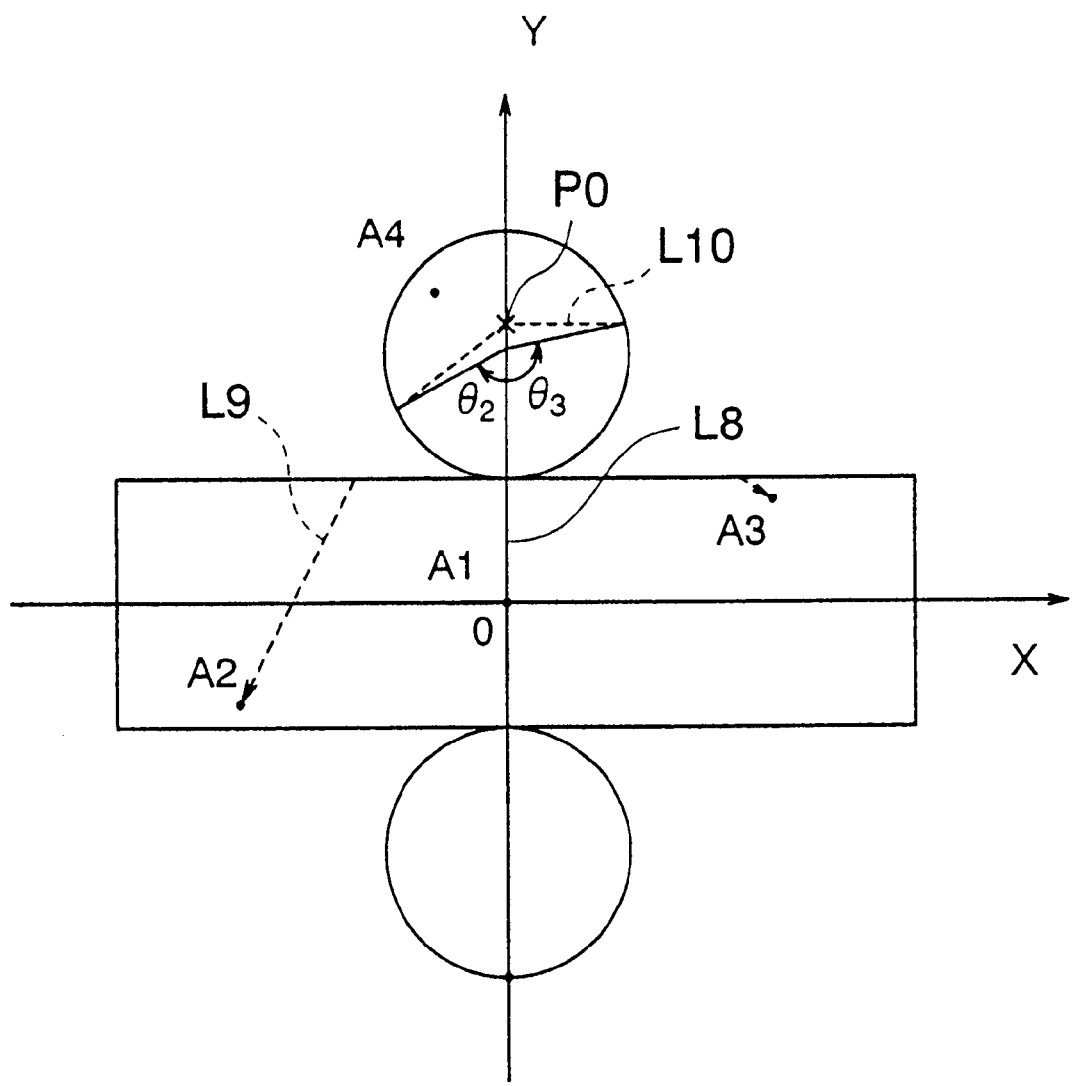
FIG. 15 shows a propagation path from the source point P0 of an anomalous discharge to an ultrasonic detector for a case where the anomalous plasma discharge has taken place on the upper end wall of a plasma processing chamber.

In step S1, if an anomalous discharge as shown in FIG. 8 is detected, the initial asymptotic point is chosen at position P0 on the upper end wall as shown in FIG. 15, assuming that the anomalous discharge source point lies on the upper end wall (block B3A). In this case, the distances from P0 to the positions A1, A2, and A3 of the ultrasonic detectors 8–10, respectively, are L8, L9, and L10 as shown in FIG. 15. The distances L9 and L10 involves angles $\theta_2$ and $\theta_3$, respectively. Therefore, the shortest distances D9 and D10 must be obtained from the distances L9 and L10, respectively.

In step S2, the shortest distances D9 and D10 are determined using the method that follows, using the distance L9 and $g_1$ given by the following respective equations.

$$L9=\sqrt{(X_{0-r\sin\theta_2})^2+(y_{0-h-t+r\cos\theta_2})^2}+\sqrt{(r\theta_{2-x_2})^2+(h-y_2)^2} \tag{10}$$

$$g_1=\partial L9/\partial\theta_2 \tag{11}$$

First, the value $g_{10}$ of $g_1$ is determined for the initial value of $\theta_2=\theta_{20}$. Next, the value $g_{11}$ of $g_1$ is determined for the angle $\theta_2$ evaluated at $\theta_{20}+\Delta\theta_{20}$, which gives the following results.

$$g(\theta)=g_1=g_{10}$$

$$\partial g(\theta)/\partial\theta=\partial g_1/\partial\theta_2=g_{11}-g_{10}/\Delta\theta_{20}$$

Inserting these values in Eq. (8), the value $\Delta\theta_2$ of $\Delta\theta$ is obtained. If the value of $\Delta\theta_2$ is not within a predetermined range of accuracy, the angle is incremented further by $\Delta\theta_2$, to renew the value thereof, using Eq. (8). This procedure will be repeated until the magnitude of $\Delta\theta_2$ falls within the predetermined range of accuracy, when the resultant asymptotic angle $\theta_{20}-\Sigma\Delta\theta_2$ is identified as the angle $\theta$ for the path having the shortest distance. It is noted that since the distance function $L(\theta)$ may have multiple minima, different initial positions should be tried to obtain $\theta$ by the asymptotic method. Of the distances associated with these first asymptotic points, the minimum one is the true shortest distance.

Similarly, the angle $\theta_3$ for the shortest path L10 is obtained by the Newton's method. Substitution of $\theta_3$ in L9 and L10 provides the shortest distances D9 and D10 (step S2). Incidentally, the shortest distance D8 is given as the length of a straight line segment L8 between P0 and A1.

In the next step S3, the shortest distances D8$x$, D9$x$, and D10$x$ are calculated for a first asymptotic position which is a small distance $\Delta x_0$ away from the initial position in the direction of X in the same manner as in step S2. In a further step S4, the shortest distances D8$y$, D9$y$, and D10$y$ are calculated for a further position a small distance $\Delta y_0$ away from the initial position in just the same way as in step S2.

In the next step S5, the amount of shifts $\Delta x$ and $\Delta y$ for the next asymptotic position are determined from the shortest distances and the values of $f_1$ and $f_2$ obtained in steps S2–S4, as follows.

The values of $f_1$, $f_2$, $\partial f_1/\partial x$, $\partial f_1/\partial y$, $\partial f_2/\partial x$, $\partial f_2/\partial y$ evaluated at the first asymptotic position $(x_0, y_0)$ to be substituted in Eqs. (4.1) and (4.2) are determined by the following equations.

$$f_1 = D9 - D8 - T9 \times V$$

$$f_2 = D10 - D8 - T10 \times V$$

$$\partial f_1/\partial x = (D9x - D8x - (D9-D8))/\Delta x_0$$

$$\partial f_1/\partial y = (D9y - D8y - (D9-D8))/\Delta y_0$$

$$\partial f_1/\partial x = (D10x - D8x - (D10-D8))/\Delta x_0$$

$$\partial f_1/\partial y = (D10y - D8y - (D10-D8))/\Delta y_0$$

Substitution of these values in (4.1) and (4.2) yields $\Delta x$ and $\Delta y$.

As a result, a second position $(x_0-\Delta x, y_0-\Delta y)$ better (i.e. closer to the asymptotic solution) than the first asymptotic position can be obtained. In step S6, this point is checked whether or not it is on the upper end wall of the processing chamber. If it is, then the procedure proceeds to step S7, where the magnitudes of $\Delta x$ and $\Delta y$ are checked to see if the position is sufficiently close to the pertinent source point of anomalous discharge. If it is determined in step S7 that the magnitudes of $\Delta x$ and $\Delta y$ are not within the predetermined range of accuracy, the second asymptotic position is further shifted by $-\Delta x$ and $-\Delta y$ in step S8. The shifted position is then used in the estimation of $\Delta x$ and $\Delta y$ for the next asymptotic position of the source point. This procedure will be repeated until the magnitudes $\Delta x$ and $\Delta y$ fall within the predetermined range of accuracy. In step S7, if it is determined that $\Delta x$ and $\Delta y$ are within the predetermined range, the procedure proceeds to step S9 to store the asymptotic solution $x=x_0-\Sigma\Delta x$, $y=y_0-\Sigma\Delta y$ in a memory as a possible solution to be compared with other asymptotic solutions, if any.

Figure 16:
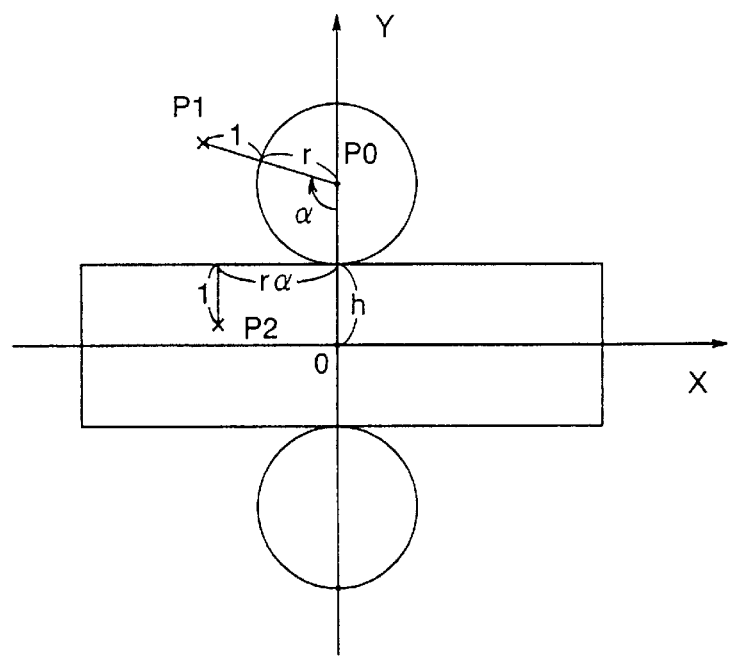
FIG. 16 shows a mapping of a calculated source point of an anomalous discharge to a point of the side wall on the XY plane for a case when the calculated source point is not on the upper end wall of the plasma processing chamber.
Figure 17:
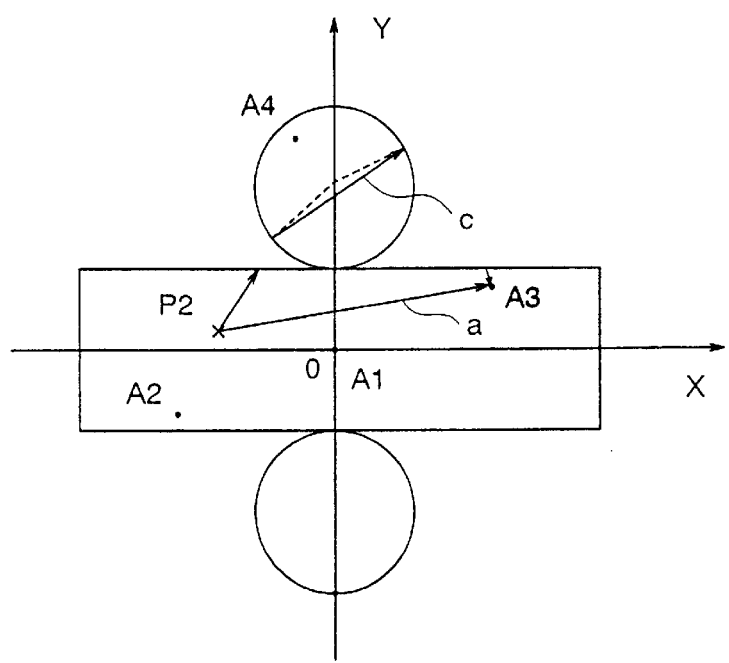
FIG. 17 shows an exemplary case where two propagation paths of an ultrasonic wave from a source point of the anomalous plasma discharge to an ultrasonic detector are conceivable.

If in step S6 the final asymptotic position is determined to be at position P1 outside the upper end wall, the procedure proceeds to step S10 (FIG. 14), where a position P2 is chosen on the side wall as the initial position for the recursive estimation to find the asymptotic solution on the side wall. The choice of P1 is made by mapping P1 to P2 such that P2 lies on the perpendicular dropped from one point of the upper end of the side wall and located at a distance r $\alpha$ from the center line of the side wall, where r is the radius of the upper end wall and $\alpha$ is the angle of the radial vector for P1, as shown in FIG. 16. The distance between the upper end of the side wall and the position P2 equals the length of the radial vector P1 minus radius r. A similar recursive estimation of the source point starting from the position P2 provides an asymptotic position closer to the source point. It should be noted that there can be more than one propagation paths, for example a direct path "a" which runs only within the side wall and a path "c" which runs across the upper end wall of the processing chamber as shown in FIG. 17. Therefore, it is necessary to determine which of the paths is actually the shortest one by calculating the lengths of the paths.

If it is determined in step S15 that the values of $\Delta x$ and $\Delta y$ obtained in step S14 provide an asymptotic position outside the side wall, then an alternative position is found by an opposite mapping as compared with the mapping used in step S10, and a determination is made in step S17 as to which sub-region the mapped position belongs to. If the mapped position is on the lower end wall, then this position is employed in step S20 as the first point of the recursive calculation for the asymptotic source point on the lower end wall. The procedure then proceeds to block 3B to obtain a final asymptotic source point on the lower end wall. If on the other hand the mapped position is not on the lower end wall, the procedure proceeds to step S21, where the position is used as the first position for the recursive calculation for the asymptotic source point on the assumption that the anomalous discharge source point lies on the upper end wall. The procedure then proceeds to step S2 of block B3$a$ to continue asymptotic determination of the source point.

In block B3$b$, a similar calculation is made to find the asymptotic source point on the lower end wall assuming the anomalous discharge source point to lie on the lower end wall, as in block B3$a$, starting from the mapped position.

After all the possible asymptotic positions of the source point are determined for the different first positions, the true asymptotic source point is determined in block B4.

It is noted that a loop is provided in the example shown in FIGS. 13 and 14 for sequentially finding alternative asymptotic source points in each of the different sub-regions when the first asymptotic source point calculated in steps S10, S20, or S21 is outside a presumed sub-region. Because of this loop, a better asymptotic source point which is closer to the true source point can be quickly found by changing the first asymptotic source point. It would be understood that a multiplicity of first asymptotic positions may be simultaneously set up (in step S1 for example) in blocks B3$a$ and B3$b$ to sequentially obtain possible asymptotic source points.

Figure 18:
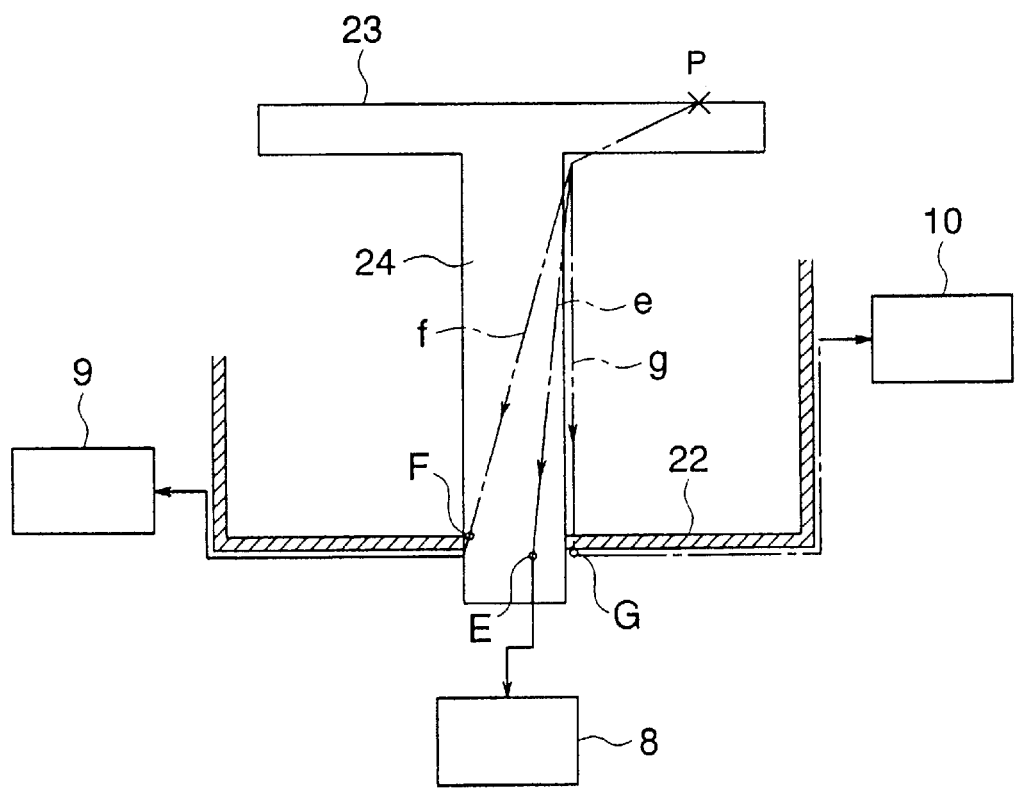
FIG. 18 is a schematic diagram showing the propagation distances of an ultrasonic wave from its source point to the respective ultrasonic detectors.

Lastly, a procedure will be described for cases where an anomalous discharge takes place on an electrode or on an electrode support. FIG. 18 shows propagation paths e, f, and g of an ultrasonic wave emitted from an anomalous discharge source point at position P on the lower electrode 23 to the respective ultrasonic detectors 8, 9, and 10. In FIG. 18, numerals 22 and 24 indicate a lower end wall and a lower electrode support, respectively. Eqs. (4.1)–(4.3) enables calculation of differences in the propagation distance from the source point to the respective detectors. The distances from the source point at P to the respective detectors 8, 9, and 10 are the distances to the points E, F, and G. These points E, F, and G are located in the neighborhood of the electrode support 24 and within a distance less than the diameter of the support 24. Since in the Newton's method the solution is obtained only approximately as the intersection of a tangent to the curve y=f(x) with X axis (y=0), the asymptotic source point on the electrode or electrode support may be determined to lie on the upper/lower end wall of the processing chamber and within a certain distance from the corresponding electrode support. For example, in the 2-dimensional coordinate system, if the anomalous discharge source point is determined to be on the electrode/ electrode support, the asymptotic source point is found on the electrodes or on the electrode support, but the precise position of the source point cannot be determined.

Figure 19A:
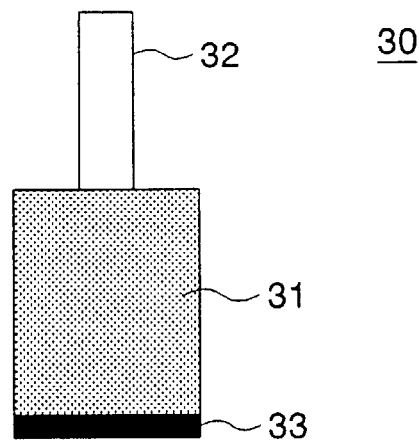
FIGS. 19A and 19B are cross sectional views of an AE sensor and an AE sensor hold case for accommodating the AE sensor of the invention, respectively.

Referring now to FIGS. 19A–22, there is shown an apparatus for mounting an ultrasonic detector of the invention. FIG. 19A shows a cross section of an AE sensor 30, which is typically an ultrasonic detector available on the market. The AE sensor 30 is adapted to detect an ultrasonic stress and convert the pressure into an electric signal. The sensor 30 includes a main body 31, an output connector 32 for outputting the electric signal, and an insulating film 33.

Figure 19B:
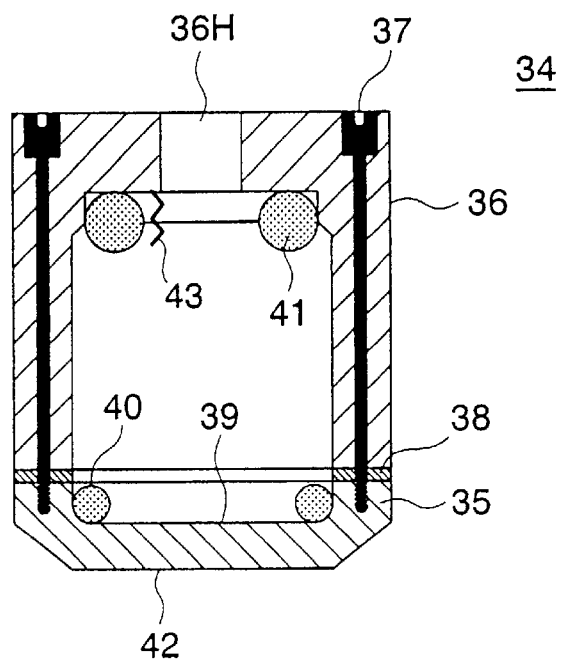

FIG. 19B shows a cross section of an AE sensor hold case 34 for housing therein the AE sensor 30 and for securely holding it in position. The AE sensor hold case 34 has a lower cover 35 and an upper cover 36. The lower case 35 has a generally planar configuration and has a convex surface one side thereof adapted to be glued onto the exterior of the processing chamber and a polished flat surface on the other side thereof to receive thereon the AE sensor. The upper cover 36 has a generally cylindrical configuration so as to cover entirely the AE sensor 30 mounted on the lower cover 35.

As shown in FIG. 19B, the upper cover 36 and the lower cover 35 are coupled together by means of coupling screws 37 via an acoustic separator in the form of a resilient packing 38. The AE sensor hold case 33 includes a couplant 39 (made of grease for example), a holding member 40 (bushing for example) for holding the AE sensor 30 at a predetermined position on the lower cover 35, a resilient shock absorbing member 41 such as an O-ring and a spring, and an insulation coat 42 such as alumite. The upper cover 36 has an opening 36H for leading the output connector of the AE sensor out of the sensor hold case, and a conductive contact 43 for keeping the upper cover 36 and the AE sensor 30 at the same electric potential.

Figure 20:
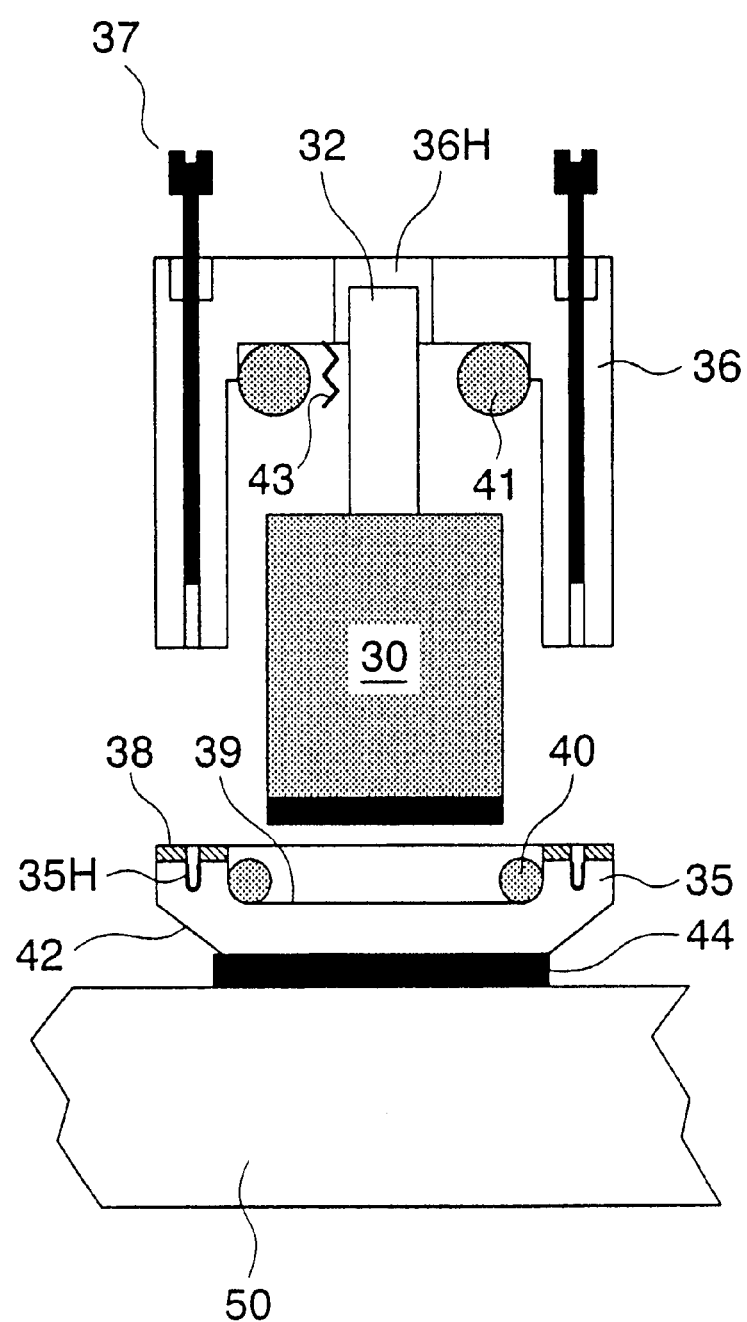
FIG. 20 shows a method of installing an AE sensor in an AE sensor hold case of the invention.
Figure 21:
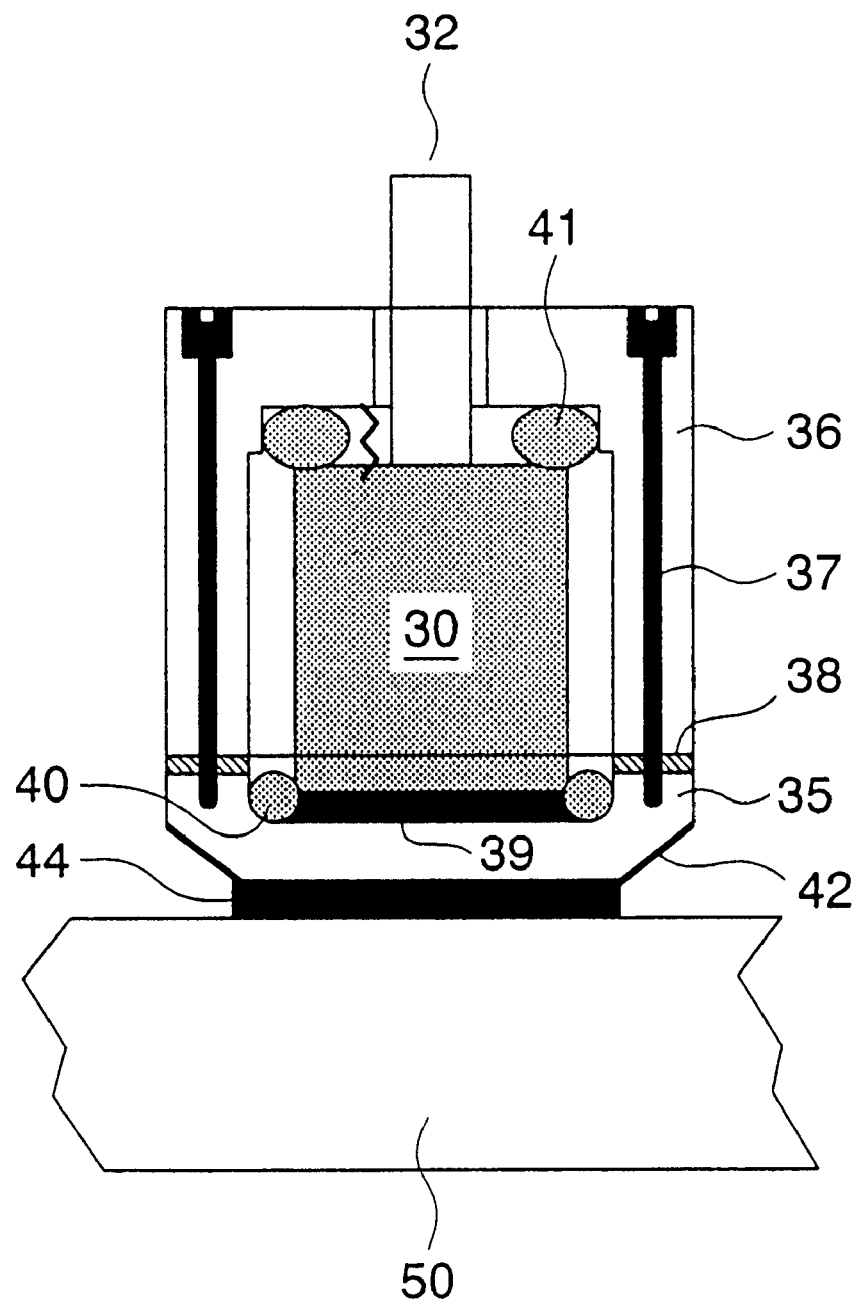
FIG. 21 is a cross sectional view of an AE sensor accommodated in an AE sensor hold case of the invention.

FIGS. 20 and 21 illustrate how the AE sensor of the invention is installed in the AE sensor hold case 34. Particularly, FIG. 20 shows a process of mounting the AE sensor in the case, and FIG. 21 a final condition of the AE sensor thus mounted. Also shown in FIGS. 20 and 21 are threaded bores 35H for receiving the screws 37, and a fixing glue (epoxy glue) 44 for fixing the AE sensor hold case on the exterior 50 of the processing chamber.

First, the lower cover 35 of the AE sensor hold case 33 is securely fixed at an appropriate exterior section 50 of the processing chamber 13 with glue 44. The lower surface of the lower cover 35 is adequate configured to fit on the exterior wall of the processing chamber 13, so that it can be easily glued on the wall. The AE sensor hold case 33 is insulated by the insulation coat 42. Next, the insulative film 33 of the AE sensor 30 is inserted in the holding member 40, the output connector 32 into the opening 36H of the upper cover 36, and coupling screws 37 into the threaded bores 35h formed in the lower cover 35 to firmly secure the upper cover 36 to the lower cover 35.

The holding member 40 can be a rubber bushing in the form of O-ring for example, adapted to hold the AE sensor 30 in position on the lower cover 35 and prevent the AE sensor 30 from contacting the upper cover 36 while mounting the AE sensor 30 on the lower cover 35. The resilient member 41 serves to prevent direct contact of the AE sensor 30 with the upper cover 36 thereby preventing the ultrasonic stress that has entered the upper case 36 via the coupling screws 37 from further propagating to the AE sensor. The resilient member 41 also serves to adequately keep the AE sensor of the upper cover 35 in forced contact with the couplant 39, thereby causing the ultrasonic wave entering the case to be efficiently transmitted to the AE sensor 30. The insulation coat 42 is provided to maintain electric insulation between the AE sensor hold case 33 and the plasma processing equipment when the former case is mounted on the exterior of the latter apparatus. The electric contacts 43 can be a metallic spring adapted to securely hold the upper and the lower covers in electric contact when they are coupled together, thereby bringing them to the same electric potential and hence reducing electric noise which is otherwise detected by the AE sensor 30. The acoustic insulation member 37 is provided to prevent the propagation of the ultrasonic wave traveling in the wall of the processing chamber into the upper cover 36 and possible resonance of the AE sensor hold case 33 caused by the ultrasonic wave.

Figure 22:
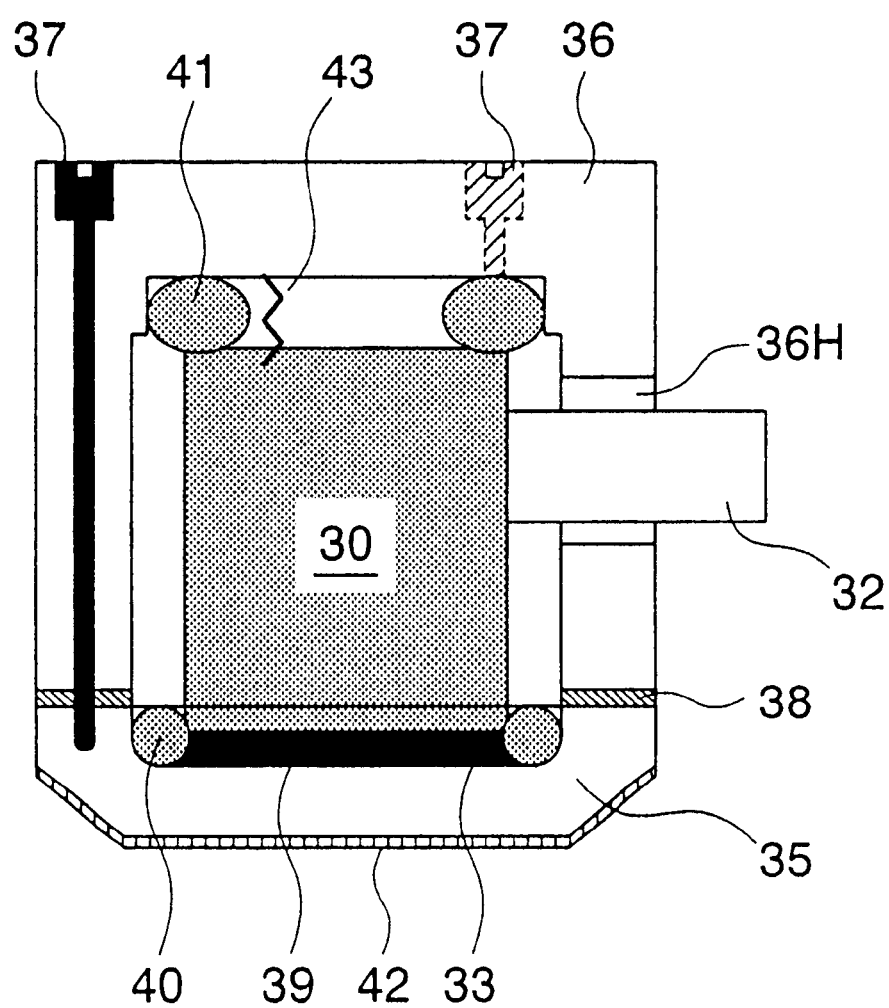
FIG. 22 is a cross sectional view of another AE sensor hold case of the invention.

FIG. 22 is a cross sectional view of the AE hold sensor case 33 which has in the side wall thereof the opening 36H for leading the output connector 32 of the AE sensor 30 out of the case 33, instead of leading the output connector 32 through the upper end of the case as shown in FIG. 19A.

INDUSTRIAL APPLICABILITY

Briefly stated, anomalous plasma discharges can be quickly and accurately detected using a method and an apparatus according to the invention. The position of an anomalous plasma discharge in a plasma processing equipment can be located by measuring and comparing on the same time axis the delay times in the propagation of the ultrasonic wave accompanying the anomalous plasma discharge, using a multiplicity of ultrasonic detectors (e.g. AE sensors) arranged on a vacuum chamber and/or discharge electrodes of the plasma processing equipment. Accordingly, occurrence of an anomalous discharge during a plasma processing and the magnitude (intensity) of the acoustic shock (AE) caused by the anomalous discharge can be automatically and accurately detected, which permits automated control of the plasma processing equipment and hence prevents production of defective products.

In addition to the merit that the locations of an anomalous plasma discharge can be accurately determined and hence that quick recovery of damage caused by the anomalous discharges is possible if any, the invention allows positive prevention of occurrence of such anomalous plasma discharges, thereby permitting efficient management of the plasma processing equipment, especially of consumable parts of the apparatus. It would be appreciated that the invention can be applied to the detection of anomalous discharge in RF plasmas and detection of anomalous sparks and arcs in DC plasmas of DC sputters as well.

As described above, anomalous plasma discharges can be detected and evaluated by a delay time-distance relationship, from the measurements of the delay times by four ultrasonic detectors mounted in or on a plasma processing equipment.

It should be appreciated that the invention has a great flexibility to reduce the installation cost of the anomalous discharge detection apparatus in that the four sensors can be of any type and placed at arbitrary positions.

An AE sensor hold case of the invention is a dedicated case which is designed to be acoustically coupled with the AE sensors mounted on the lower cover, which is glued to the wall of a processing chamber so that ultrasonic waves propagating from an anomalous discharge to the lower cover can be efficiently detected by the AE sensors. The use of such dedicated case provides a simple and safe way of mounting/dismounting the AE sensors for maintenance without suffering from destruction and deterioration during mounting/dismounting, and hence maintain precision of the AE sensors.

What is claimed:

1. An anomalous arc discharge detection apparatus for use with a plasma processing equipment, comprising:
    a plasma chamber;
    first and second electrodes arranged in said plasma chamber;
    a high frequency power source connected to said first electrode for generating a weakly-ionized thermal non-equilibrium plasma in said chamber;
    a multiplicity of ultrasonic detection means for detecting ultrasonic waves accompanying an anomalous arc discharge in said plasma processing equipment, and for generating signals indicative of the ultrasonic wave detected;
    data processing means for processing waveforms of said ultrasonic wave signals; and
    monitor means for displaying a signal indicative of said anomalous discharge.

2. The anomalous arc discharge detection apparatus according to claim 1, wherein
    said multiplicity of ultrasonic detection means are mounted on predetermined sections of said plasma processing equipment, and
    said data processing means is adapted to determine the location of an anomalous arc discharge based on the propagation time differences of said ultrasonic wave from said source point to the respective multiple ultrasonic detection means.

3. The anomalous arc discharge detection apparatus according to claim 2, wherein said ultrasonic detection means are provided with electrically insulated mounting means for mounting said ultrasonic detection means on said plasma processing equipment in an electrically insulated condition.

4. The anomalous arc discharge detection apparatus according to claim 3, further comprising:
    means for determining the level of an anomalous event (AE) generating an ultrasonic wave by processing waveforms of said ultrasonic wave processed by said data processing means; and
    means for generating an alarm for issuing an alarm when said level exceeds a given threshold.

5. The anomalous arc discharge detection apparatus according to claim 4, wherein said ultrasonic detection means are provided with electrically insulated mounting means for mounting said ultrasonic detection means on said plasma processing equipment in an electrically insulated condition.

6. The anomalous arc discharge detection apparatus according to claim 2, comprising four ultrasonic detection means, installed on the walls of said plasma processing chamber, for use in the determination of the location of said source point by an asymptotic approximation method.

7. The anomalous arc discharge detection apparatus according to claim 1, further comprising:
    means for determining the level of an anomalous event (AE) generating an ultrasonic wave by processing waveforms of said ultrasonic wave processed by said data processing means; and
    means for generating and issuing an alarm when said level exceeds a given threshold.

8. The anomalous arc discharge detection apparatus according to claim 7, wherein said ultrasonic detection means are provided with electrically insulated mounting means for mounting said ultrasonic detection means on said plasma processing equipment in an electrically insulated condition.

9. A method of detecting an anomalous arc discharge in a plasma processing equipment, comprising steps of:
    mounting four ultrasonic detection means at predetermined positions of said plasma processing equipment; and
    locating the source point of said anomalous arc discharge based on the propagation time differences of an ultrasonic wave propagating from said source point to the respective multiple ultrasonic detection means.

10. The method of detecting an anomalous arc discharge according to claim 9, wherein said method uses four ultrasonic detection means, and said step of locating the anomalous arc discharge is an asymptotic approximation of the position of said source point through recursive calculations of the distances between said source point to the respective ultrasonic detection means from said propagation time differences, using known relationships between said distances and said propagation time differences.

11. An acoustic sensor hold case for accommodating an AE sensor, said hold case having one side to be glued onto an exterior of a processing chamber of a plasma processing equipment, said hold case comprising:
    a generally slab shaped lower cover having a polished flat inner surface for acoustically coupling said one side with said AE sensor;
    a generally cylindrical upper cover for enclosing said AE sensor, wherein
    said upper and lower covers are configured to be connected together by screws to firmly secure said AE sensor in position in said hold case so that the input end of said AE sensor is abutted against said inner surface of said lower cover with an adequate pressure, providing acoustic coupling therebetween.

12. The acoustic sensor hold case according to claim 11, further comprising at an inner upper position of said upper cover a resilient member which causes said input end of said AE sensor abuts against a couplant coated on the inner surface of said lower cover with an adequate pressure when said upper and the lower covers are coupled together.

13. The acoustic sensor hold case according to claim 11, wherein only said one end of said AE sensor hold case is covered with an electrically insulative film.

14. The acoustic sensor hold case according to claim 11, further comprising at an inner upper section of said upper case an electrically conductive contact which abuts against said AE sensor, thereby bringing said AE sensor and said upper case to the same electric potential when said upper and lower covers are coupled together.

15. The acoustic sensor hold case according to claim 11, further comprising an acoustically insulative member between the contacting surfaces of said upper and lower covers.

16. The acoustic sensor hold case according to claim 11, wherein said upper cover is provided in either the upper end or the side wall thereof with an opening for passing therethrough an output connector of said AE sensor.

17. The acoustic sensor hold case according to claim 11, further comprising a rubber bushing lying along the inner periphery of said lower cover and extending along the external periphery of said AE sensor such that said bushing keeps said AE sensor not in direct contact with said upper cover when said upper and lower covers are coupled together.

18. An anomalous arc discharge detection apparatus for use with a plasma processing equipment, comprising:

a multiplicity of ultrasonic detection means for detecting ultrasonic waves accompanying an anomalous arc discharge in said plasma processing equipment, and for generating ultrasonic wave signals indicative of the ultrasonic waves detected;

data processing means for processing waveforms of said ultrasonic wave signals;

monitor means for displaying a signal indicative of said anomalous discharge;

electrically insulated mounting means for mounting said ultrasonic detection means on said plasma processing means in an electrically insulated condition.

19. A plasma processing apparatus comprising:

a plasma chamber;

first and second electrodes arranged in said plasma chamber;

a high frequency power source connected to said first electrode for generating a plasma in said chamber;

an ultrasonic detector for detecting ultrasonic waves created by said plasma and for generating ultrasonic signals indicative of the ultrasonic waves detected;

a data processor connected to said ultrasonic detector for processing said ultrasonic wave signals to identify an anomalous arc discharge in said chamber.

20. An apparatus in accordance with claim 19, wherein:

the plasma generated by said high frequency power source and said electrodes in said chamber, is capable of chemical vapor deposition (CVD), ashing, etching, and sputtering of a semiconductor substrate, as well as surface processing thereof.

21. An apparatus in accordance with claim 19, wherein:

the plasma generated by said high frequency power source and said electrodes in said chamber, is for chemical vapor deposition (CVD), ashing, etching, and sputtering of semiconductor substrates, as well as for surface processing thereof.

22. An apparatus in accordance with claim 19, wherein:

said high frequency power source and said electrodes generate a plasma in said chamber used in chemical vapor deposition (CVD), ashing, etching, and sputtering of semiconductor substrates.

23. An apparatus in accordance with claim 19, wherein:

said high frequency power source and said electrodes generate a weakly-ionized thermal non-equilibrium plasma in said chamber.

24. A method for operating a plasma processing apparatus, the method comprising the steps of:

providing a plasma chamber with first and second electrodes arranged in said plasma chamber;

applying high frequency electrical energy to said first electrode to generate a plasma in said chamber;

measuring ultrasonic waves from said chamber created by said plasma;

generating ultrasonic signals indicative of the ultrasonic waves detected;

processing said ultrasonic wave signals to identify an anomalous arc discharge in said chamber.

25. A method in accordance with claim 24, wherein:

said applying of said high frequency electrical energy to said first electrode generates a weakly-ionized thermal non-equilibrium plasma in said chamber.

26. A method in accordance with claim 24, further comprising:

using said plasma for chemical vapor deposition (CVD), ashing, etching, and sputtering of a semiconductor substrate.

* * * * *